US012674195B2

(12) United States Patent
Wang et al.

(10) Patent No.: US 12,674,195 B2
(45) Date of Patent: *Jul. 7, 2026

(54) METHODS AND KITS FOR HIGHLY MULTIPLEX SINGLE PRIMER EXTENSION

(71) Applicant: QIAGEN SCIENCES, LLC, Germantown, MD (US)

(72) Inventors: Yexun Wang, Ellicott City, MD (US); Quan Peng, Clarksburg, MD (US)

(73) Assignee: QIAGEN Sciences, LLC, Germantown, MD (US)

( * ) Notice: Subject to any disclaimer, the term of this patent is extended or adjusted under 35 U.S.C. 154(b) by 423 days.

This patent is subject to a terminal disclaimer.

(21) Appl. No.: 17/162,571

(22) Filed: Jan. 29, 2021

(65) Prior Publication Data

US 2021/0301333 A1     Sep. 30, 2021

Related U.S. Application Data

(63) Continuation of application No. 15/767,312, filed as application No. PCT/US2016/057073 on Oct. 14, 2016, now Pat. No. 10,941,438.

(60) Provisional application No. 62/242,766, filed on Oct. 16, 2015.

(51) Int. Cl.
| | |
|---|---|
| *C12Q 1/68* | (2018.01) |
| *C12N 9/12* | (2006.01) |
| *C12Q 1/6844* | (2018.01) |
| *C12Q 1/6848* | (2018.01) |
| *C12Q 1/686* | (2018.01) |
| *C12Q 1/6869* | (2018.01) |

(52) U.S. Cl.
CPC ......... *C12Q 1/6848* (2013.01); *C12N 9/1252* (2013.01); *C12Q 1/6844* (2013.01); *C12Q 1/686* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 5,877,280 A | 3/1999 | Wetmur | |
| 6,150,112 A | 11/2000 | Weissman et al. | |
| 6,287,825 B1 | 9/2001 | Weissman et al. | |
| 2003/0170649 A1* | 9/2003 | Haas ................... | C12Q 1/6827 |
| | | | 435/6.12 |
| 2007/0190531 A1* | 8/2007 | Mitani ................. | C12Q 1/6816 |
| | | | 435/6.12 |
| 2008/0044921 A1 | 2/2008 | Iwaki et al. | |
| 2011/0236900 A1* | 9/2011 | Hayashizaki ........ | C07K 14/195 |
| | | | 435/243 |
| 2014/0211204 A1* | 7/2014 | Stedtfeld ................ | C12Q 1/686 |
| | | | 250/206 |

FOREIGN PATENT DOCUMENTS

| | | | |
|---|---|---|---|
| WO | 98/01562 A1 | 1/1998 | |
| WO | 2007/123742 A2 | 11/2007 | |
| WO | 2013/175815 A1 | 11/2013 | |
| WO | WO-2014071218 A2 * | 5/2014 | ........... C12Q 1/6886 |

OTHER PUBLICATIONS

Fukui, K. et al. Thermostable mismatch-recognizing mismatch protein MutS suppresses nonspecific amplification during polymerase chain reaction. Int. J. Mol. Sci., vol. 14, p. 6436-6453, (2013).*

Zhao G., et al. Polymerization behavior of Klenow fragment and Taq DNA polymerase in short primer extension. Acta Biochim Biophys Sin, vol. 42, p. 722-728, (2010).*

"Bisulfite sequencing," Wikipedia, archived Nov. 2, 2017, URL= https://en.wikipedia.org/w/index.php?title=Bisulfite_sequencing &oldid=808370619, download date Jul. 11, 2018, 12 pages.

Altshuler, "PCR Troubleshooting," URL=http://www.highveld.com/ pcr/pcr-troubleshooting.html, download date Jul. 11, 2018, 5 pages.

Biswas et al., "Identification and Characterization of a Thermostable MutS Homolog from *Thermus aquaticus*," *The Journal of Biological Chemistry 271*(9):5040-5048, 1996. (10 pages).

Brotherton et al., "Single primer extension (SPEX) amplification to accurately genotype highly damaged DNA templates," *Forensic Science International: Genetics Supplement Series 1*(1):19-21, 2008.

Eisen, "A phylogenomic study of the MutS family of proteins," *Nucleic Acids Research 26*(18):4291-4300, 1998.

Fukui et al., "Thermostable Mismatch-Recognizing Protein MutS Suppresses Nonspecific Amplification during Polymerase Chain Reaction (PCR)," *Int. J. Mol. Sci. 14*:6436-6453, 2013.

Mitani et al., "Rapid SNP diagnostics using asymmetric isothermal amplification and a new mismatch-suppression technology," *Nature Methods 4*(3):257-262, 2007.

Myllykangas et al., "Efficient targeted resequencing of human germline and cancer genomes by oligonucleotide-selective sequencing," *Nature Biotechnology 29*(11):1024-1027, 2011. (26 pages).

Peng et al., "Reducing amplification artifacts in high multiplex amplicon sequencing by using molecular barcodes," *BMC Genomics 16*:589, 2015. (12 pages).

Primrose et al., *Principles of Gene Manipulation and Genomic*, 7th ed., Blackwell Publishing, Hoboken, New Jersey, USA, 2005, Chap. 8, "Changing genes: site-directed mutagenesis and protein engineering," pp. 141-156.

Rizzi et al., "Ancient DNA studies: new perspectives on old samples," *Genetics Selection Evolution 44*:21, 2012. (19 pages).

Stanisławska-Sachadyn et al., "MutS as a tool for mutation detection," *Acta Biochimica Polonica 52*(3):575-583, 2005.

(Continued)

*Primary Examiner* — Suryaprabha Chunduru
(74) *Attorney, Agent, or Firm* — Seed Intellectual Property Law Group LLP

(57)     ABSTRACT

The present disclosure provides methods and kits for highly multiplex single primer extensions using a MutS protein and $Mg^{2+}$ at a concentration higher than that in a typical PCR reaction. Also disclosed is the use of such methods and kits in next generation sequencing.

19 Claims, 4 Drawing Sheets

Specification includes a Sequence Listing.

(56)                 References Cited

OTHER PUBLICATIONS

Watanabe et al., "Use of a competitive probe in assay design for genotyping of the UGT1A1*28 microsatellite polymorphism by the smart amplification process," *BioTechniques* 43(4):479-484, 2007.

* cited by examiner

1. DNA random fragmentation

2. Library construction with NGSCounter

3. Single primer extension

4. Universal PCR library

5. Library quantification

6. Sequencing

METHODS AND KITS FOR HIGHLY MULTIPLEX SINGLE PRIMER EXTENSION

CROSS REFERENCE TO RELATED APPLICATION

The present application is a continuation of U.S. application Ser. No. 15/767,312, filed Apr. 10, 2018, which is a U.S. national phase application of PCT/US2016/057073, filed Oct. 14, 2016, which claims the benefit under 35 U.S.C. § 119(e) to U.S. Provisional Application No. 62/242,766, filed Oct. 16, 2015. U.S. application Ser. No. 15/767,312 is herein incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 830109_409C1_SEQUENCE_LISTING.txt. The text file is 37.8 KB, was created on Jan. 27, 2021, and is being submitted electronically via EFS-Web.

BACKGROUND

Technical Field

The present disclosure relates to highly multiplex single primer extensions with improved efficiency and specificity and their use in next generation sequencing (NGS).

Description of the Related Art

Targeted sequencing is one of the major applications for NGS. It is a cost efficient way to sequence the most relevant portion of the genome or transcriptomes.

Highly multiplex PCR is one of the popular methods to prepare samples for targeted sequencing. Although it is a simple yet powerful tool to enrich a large gene region, it has limited ability to detect large structural variants such as gene fusion or splicing variants because the two primers per amplicon design cannot accommodate large or unknown structural changes between the two predefined primer sites. In addition, highly multiplex PCR is difficult to be scaled up to cover very large regions such as whole transcriptome or exome in a single reactions tube. The many pairs of primers will introduce unwanted artifacts when multiplex scale increases dramatically.

A recent alternative approach to enriching target loci is single primer extensions. The single primer design allows the detection of large and unknown structural variants, and improves scalability for covering very larger panels. However, because target specificity is provided by only one primer, the overall enrichment specificity is generally much lower than PCR enrichment using two target-specific primers.

One way to improve single primer specificity is to conduct the single primer annealing at more stringent conditions (e.g., at high temperature and high salt condition) and only perform polymerase extension after primer binding has reached equilibrium. However, high stringent hybridization conditions typically reduce DNA polymerase activity. In addition, performing polymerase extension after primer binding is inconvenient.

Another challenge in enriching a very large region is the limitation of each primer concentration. Because of the physical and chemical constraints, when more different primers are added in one reaction (to cover more regions), the concentration of each primer inevitably has to be lowered in proportion. For example, each primer may need to be at 2 nM when 20,000 primers are used to enrich 500 genes, while each primer may be at 20 nM when 2000 primers are used to enrich 50 genes. In other cases, the concentration is limited by how the primer is synthesized. For example, oligonucleotides prepared by massive parallel synthesis on microchip have much lower yields than by traditional column-based synthesis approach. In both scenarios, lower primer concentrations will lead to lower template annealing efficiency under standard conditions.

One way to improve annealing efficiency is to prolong the annealing time to hours, which is not very desirable. While it is possible to change the annealing chemistry to accelerate proper primer-template binding, doing so increases non-specific primer binding and extension by DNA polymerase, leading to overall low specificity.

SUMMARY

In one aspect, the present disclosure provides a method for performing a highly multiplex single primer extension reaction, comprising:

a. extending at least about 1,000 different primers in a single primer extension reaction using a plurality of target nucleic acids as templates in the presence of (1) a MutS protein, and (2) $Mg^{2+}$ at a minimum concentration of about 6 mM to generate extension products.

In certain embodiments, at least about 4,000 additional different primers, such as at least 9,000 additional different primers are extended in the single primer extension reaction.

In certain embodiments, the single primer extension reaction is performed in the absence of a primer capable of specifically annealing to a portion of the extension products.

In certain embodiments, most of the target nucleic acids comprise a common sequence, and wherein the reaction is performed in the presence of a boosting primer that comprises the common sequence or a portion thereof that is at least about 10 nucleotides in length.

In certain embodiments, each of the primers other than the boosting primer is present in the single primer extension reaction at a concentration of no more than about 20 nM.

In certain embodiments, each of the primers other than the boosting primer is present in the single primer extension reaction at a concentration of about 1 nM to about 10 nM.

In certain embodiments, $Mg^{2+}$ is present in the single primer extension reaction at a concentration of about 6 mM to about 20 mM.

In certain embodiments, the plurality of target nucleic acids are genomic DNA or amplification products of genomic DNA.

In certain other embodiments, the plurality of target nucleic acids are cDNA or amplification products of cDNA.

In certain embodiments, the plurality of target nucleic acids are bisulfite treated genomic DNA or its amplified products.

In certain embodiments, the MutS protein is a *Thermus aquaticus* MutS protein.

In certain embodiments, the primer annealing and extension specificity of the single primer extension reaction is at least about 80%.

In certain embodiments, the average primer annealing and extension efficiency of the single primer extension reaction is at least about 10%.

In certain embodiments, the method provided herein further comprises:

b. optionally amplifying the extension product(s) to generate amplified extension product(s), and c. sequencing the extension product(s) or the amplified extension products.

In certain embodiments, the target nucleic acids are partially double-stranded, and comprise a double-stranded target nucleic acid sequence and a single-stranded common sequence at the 5' terminus of each strand of the target nucleic acid sequence.

In certain embodiments, prior to step a. the method disclosed herein comprises:

(i) fragmenting DNA molecules to generate double-stranded DNA fragments, and (ii) ligating the single-stranded common sequence to the 5' terminus of each strand of the double-stranded DNA fragment to provide partially double-stranded target nucleic acids.

In certain embodiments, each primer other than the boosting primer if present comprises at its 5' terminus a universal sequence that is incapable of specifically annealing to a region of a target nucleic acid.

In a related aspect, the present disclosure provides a method for sequencing nucleic acids, comprising:

a. providing a plurality of partially double-stranded target nucleic acids each of which comprises a double-stranded target nucleic acid sequence, and a single-stranded common sequence at the 5' terminus of each strand of the target nucleic acid sequence, wherein the single-stranded common sequence is the same among the plurality of the target nucleic acids;

b. providing a plurality of primers capable of specifically annealing to portions of the target nucleic acid sequences;

c. extending the primers using the target nucleic acid sequences as templates in the presence of (1) a MutS protein and (2) $Mg^{2+}$ at a minimum concentration of about 6 mM to obtain extension products; and d. sequencing the extension products or their amplification products.

In certain embodiments, extending the primers in step c. is performed in the presence of a boosting primer comprising the common sequence or a portion thereof that is at least about 10 nucleotides in length.

In certain embodiments, step a. comprises:

a1. fragmenting double-stranded DNA molecules to generate double-stranded DNA fragments, and a2. ligating the single-stranded common sequence to the 5' terminus of each strand of the double-stranded DNA fragments to provide the plurality of partially double-stranded nucleic acids.

In certain embodiments, the method comprises: prior to step d., a further step of amplifying the extension products of step c.

In another aspect, the present application provides a kit for performing a primer extension reaction, comprising:

(1) a pool of at least about 1,000 different primers, (2) a buffer concentrate comprising a MutS protein, dNTPs, and $Mg^{2+}$, wherein the concentration of $Mg^{2+}$ in a highly multiplex single primer extension reaction mixture generated from diluting the buffer concentrate is at least about 6 mM, and (3) a DNA polymerase.

In certain embodiments, the kit comprises a pool of at least about 10,000 different primers.

In certain embodiments, the MutS protein is a *Thermus aquaticus* MutS protein.

DETAILED DESCRIPTION

Figure 1:
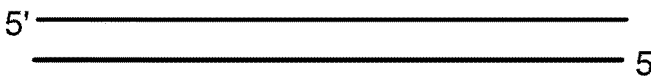
FIG. 1 is a schematic representation of an embodiment of the present disclosure, showing that single primer extension is used in sequencing.
Figure 1:
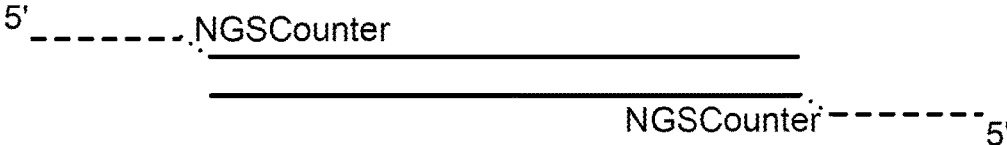
Figure 1:
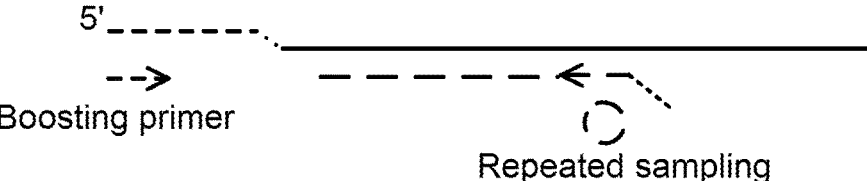
Figure 1:
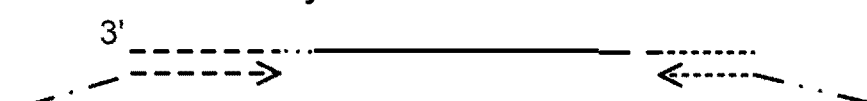

Targeted sequence enrichment using single primer extension approach has great advantages over traditional two primer PCR amplicon based enrichment. Because one boundary of the amplified product is not constrained by one predefined primer, it has the ability to detect unexpected structural variations in the sequence, such as fusions and splicing variants. However, due to only one primer being used, single primer extension has traditionally suffered from low enrichment specificity. Another challenge in target enrichment is the low primer annealing efficiency especially when the primer concentration is low to accommodate large gene panels. Existing approaches to promoting primer binding typically inadvertently reduce binding specificity.

Faced with the challenges of low primer annealing efficiency and specificity, the present inventors have identified a solution to increasing primer annealing extension efficiency while improving primer extension specificity via a combination of $Mg^{2+}$ at a concentration higher than in a typical PCR reaction and a MutS protein. This combination is especially beneficial when a large number of very low concentrations of primers are used in single primer extension process to enrich a large genomics region for sequencing analysis.

In the following description, any ranges provided herein include all the values in the ranges. It should also be noted that the term "or" is generally employed in its sense including "and/or" (i.e., to mean either one, both, or any combination thereof of the alternatives) unless the content dictates otherwise. Also, as used in this specification and the appended claims, the singular forms "a," "an," and "the" include plural referents unless the content dictates otherwise. The terms "include," "have," "comprise" and their variants are used synonymously and to be construed as non-limiting. The term "about" refers to ±10% of a reference value. For example, "about 50° C." refers to "50° C.±5° C." (i.e., 50° C.±10% of 50° C.).

I. Methods for Performing Single Extension Reactions

In one aspect, the present disclosure provides a method for performing a highly multiplex single primer extension reaction that comprises extending at least about 1,000 different primers in a single primer extension reaction using a plurality of target nucleic acids as templates in the presence of (1) a MutS protein, and (2) Mg$^{2+}$ at a minimum concentration of about 6 mM to generate extension products.

The term "single primer extension" or "single primer extension reaction" as used in the present disclosure refers to a reaction in which a primer is extended using a single-stranded target nucleic acid or one strand of a double-stranded target nucleic acid as a template. A single primer extension does not include extension of another primer that anneals to the complementary strand of the single-stranded target nucleic acid or the other strand of the double-stranded target nucleic acid except where a boosting primer is used as described below.

A "primer" is an oligonucleotide capable of specifically annealing to a target nucleic acid, which allows the extension of the primer using the target nucleic acid as a template. Generally, such a primer or a sufficiently long portion thereof (e.g., at least about 10, 11, 12, 13, 14, or 15 nucleotides long) is substantially or completely complementary to a region the target nucleic acid to allow specific annealing of the primer to the target nucleic acid. A primer used in a multiplex single primer extension reaction as disclosed herein for targeted nucleic acid enrichment may also be referred to as an "enrichment primer."

An "oligonucleotide" refers to a short polymer composed of deoxyribonucleotides, ribonucleotides or combinations thereof. Oligonucleotides are generally between about 10 to about 100 nucleotides, preferably about 12 to about 60 nucleotides, in length.

The terms "complementary" and "complement" and their variants, as used herein, refer to any two nucleic acid sequences or portions thereof that form a hybridized duplex by base pairing. One nucleic acid fragment may be completely complementary to another nucleic acid fragment if all of the nucleotides in the fragment form base pairing with nucleotides in the corresponding antiparallel positions on the other nucleic acid fragment. A primer (or a portion thereof that is at least about 10 nucleotides in length) is "substantially complementary" to a target nucleic acid if at least 90% (e.g., at least 95%, at least 98%, or at least 99%) of the residues of the primer (or the portion thereof) are complementary to corresponding residues in the target nucleic acid over the length of the primer (or the portion thereof).

In certain embodiments, a primer is substantially or completely complementary to a target nucleic acid over the complete length of the primer. In certain other embodiments, a primer is not substantially complementary to a target nucleic acid over the complete length of the primer. In such embodiments, the primer may comprise a sequence at its 3' end that is substantially or completely complementary to the target nucleic acid so that the primer may specifically anneal to the target nucleic acid, and another sequence at its 5' end that is not substantially complementary to the target nucleic acid sequence.

A single primer extension reaction may include multiple cycles of annealing of a primer to a single-stranded target nucleic acid or a strand of a double-stranded target nucleic acid, extending the primer, and denaturing the extension product from its complementary template to increase the amount of extension product.

In certain embodiments, the single primer extension reaction does not comprise any primer capable of specifically annealing to the complementary strand of the single-stranded target nucleic acid or the other strand of the double-stranded target nucleic acid. In such embodiments, multiple cycles of annealing, extending, and denaturing lead to linear amplification of the extension product.

A primer is capable of specifically annealing to a template nucleic acid if the primer is substantially or completely complementary to the template nucleic acid or a portion thereof that is at least about 10 nucleotides in length.

In certain other embodiments, the single primer extension reaction comprises a boosting primer. As discussed below, including a boosting primer in a single primer extension reaction that comprises multiple cycles of denaturing, annealing and extending will lead to exponential amplification of the extension product.

A "multiplex single primer extension reaction" is a single primer extension reaction where a plurality of primers (also referred to as "a primer set" or "a pool of primers") other than a boosting primer as described below are extended using one or more target nucleic acids as templates.

A "highly multiplex single primer extension reaction" refers to a multiplex single primer extension reaction where at least about 1,000 different primers other than a boosting primer are extended using a plurality of target nucleic acids as templates.

In certain embodiments, a highly multiplex single primer extension reaction may contain about 1,000 to about 100,000 different primers. For example, a highly multiplex single primer extension may contain at least about 1,000, 1,500, 2,000, 2,500, 3,000, 3,500, 4,000, 4,500, or 5,000 different primers, and/or at most about 10,000, 20,000, 30,000, 40,000, 50,000, 60,000, 70,000, 80,000, 90,000, or 100,000 different primers, including any combination of the above-noted minimum and maximum numbers of different primers such as about 1,000 to about 10,000, about 1,000 to about 50,000, about 1,000 to about 100,000, about 5,000 to about 20,000, about 5,000 to about 50,000, or about 5,000 to about 100,000 different primers.

In a highly multiplex single primer extension reaction, primers other than a boosting primer (if present) may anneal to different genes, different regions of the same genes, and/or different strands of the same regions of the same genes as long as none of such primers forms a pair with another primer in the same reaction that allows exponentially amplification of a portion of a target nucleic acid delineated by the primer pair. In cases where two primers in a multiplex single primer extension reaction anneal to different portions of the same strand of a target nucleic acid, preferably, the different portions are sufficiently apart from each other so that the extension of one primer does not interfere with the extension of the other primer.

In certain embodiments, each primer other than a boosting primer (if present) in a highly multiplex single primer extension reaction comprises at its 5' terminus a universal sequence that is incapable of specifically annealing to a region of a target nucleic acid. Such a universal sequence is useful in designing additional primers for amplifying the products of the highly multiplex single primer extension reaction. Additional description of such a universal sequence is provided in Section II below.

The primers may be obtained in any methods known in the art for synthesizing oligonucleotides. In certain embodiments, the primers are synthesized on microchips.

In a multiplex single primer extension reaction, the initial concentration (i.e., the concentration at the start of the single primer extension reaction) of each primer other than a boosting primer may be about 0.01 nM to about 100 nM, preferably about 1 nM to about 40 nM, such as about 2 nM to about 20 nM.

In certain embodiments, each primer other than a boosting primer in a multiplex single primer extension reaction has an initial concentration of at least about 0.01, 0.02, 0.03, 0.04, 0.05, 0.06, 0.07, 0.08, 0.09, 0.1, 0.2, 0.3, 0.4, or 0.5 nM and/or at most about 1, 2, 3, 4, 5, 6, 7, 8, 9, 10, 11, 12, 13, 14, 15, 16, 17, 18, 19, 20, 30, 40, 50, 60, 70, 80, 90, or 100 nM, including any combination of the above-noted minimum and maximum concentrations.

Target nucleic acids useful as templates in single primer extension reactions disclosed herein may be any nucleic acids of interest, including genomic DNA, cDNA, genomic DNA treated with bisulfite, and the amplification products of the above-noted nucleic acids.

Target nucleic acids may be single-stranded, double-stranded, or partially double-stranded. In certain embodiments, target nucleic acids are partially double-stranded and comprise a double-stranded target nucleic acid sequence and a single-stranded common sequence at the 5' terminus of each strand of the target nucleic acid sequence. The single-stranded common sequence is the same among the target nucleic acids, and allows the design of a boosting primer as described below to increase or maximize the yield of extension products.

Target nucleic acids may be isolated from any samples, sources, or organisms of interest that contain nucleic acids, including materials obtained from clinical, forensic, and environmental settings. Preferably, the sample is a biological sample derived from a human, animal, plant, bacteria or fungi. The term "sample" also includes processed samples including preserved, fixed and/or stabilized samples, such as formalin fixed and paraffin-embedded (FFPE samples) and other samples that were treated with cross-linking fixatives such as glutaraldehyde.

Exemplary samples from which nucleic acids may be prepared include, but are not limited to, blood, swabs, body fluid, tissues including but not limited to, liver, spleen, kidney, lung, intestine, brain, heart, muscle, and pancreas, cell cultures, food samples, plant tissues or samples, as well as lysates, extracts, or materials and fractions obtained from the samples described above, or any cells, microorganisms and viruses that may be present on or in a sample, and the like.

Isolating target nucleic acids from a sample of interest may be performed by any method known in the art useful for nucleic acid isolation or purification. In addition, many kits for nucleic acid preparation are commercially available and may be used, including QIAamp DNA mini kit, QIAamp FFPE Tissue kit, and PAXgene DNA kit.

Alternatively, target nucleic acids useful as templates in single primer extension reactions disclosed herein may be obtained by modifying nucleic acids isolated from a sample. For example, in certain embodiments, target nucleic acids may be generated by (i) fragmenting DNA molecules (e.g., genomic DNA) to obtain double-stranded DNA fragments, and (ii) ligating a single-stranded common sequence to the 5' terminus of each stand of the double-stranded DNA fragments.

As indicated above, in certain embodiments, a single primer extension reaction may further comprise a boosting primer. A boosting primer may be included in a multiplex single primer extension reaction where most (i.e., at least about 90%, such as at least about 95%, about 98% or about 99%) or all of target nucleic acids each comprise a common sequence. The boosting primer comprises the common sequence or a portion thereof that is at least about 10 nucleotides in length, and is thus able to specifically anneal to a nucleic acid strand that comprises the complement of the common sequence and be extended using such a strand as a template in the single primer extension reaction. Thus, the presence of a boosting primer allows exponential amplification of target nucleic acids. However, because it comprises a sequence common to most or all of target nucleic acids, it does not affect specificity of the amplification. An exemplary use of a boosting primer is shown in FIG. 1 as described below in detail.

The initial concentration of a boosting primer may be from about 10 nM to about 10 mM, preferably from about 100 nM to about 2 mM, such as about 200 nM to about 600 nM.

Single primer extension reactions disclosed herein are performed in the presence of a MutS protein.

A MutS protein is a protein that binds to heteroduplex DNA containing mispaired or unpaired bases or a small DNA insertion/deletion loops of one to a few (e.g., 2, 3, 4, or 5) nucleotides and has sequence homology with *Escherichia coli* MutS protein (GenBank Accession No. GI: 127556, SEQ ID NO:1). It includes members of the MutS family described in Eisen, Nucleic Acids Research 26: 4291-4300, 1998, especially those in the MutS-I lineage.

In certain embodiments, the MutS protein is thermostable, that is, capable of at least partially maintaining (e.g., at least about 10%, about 20%, about 30%, about 40%, or about 50% of) its activity of binding to heteroduplex DNA containing mispaired or unpaired bases or a small DNA insertion/deletion loop of one to a few nucleotides at a temperature of at least about 50° C., such as at least about 60° C., about 70° C., about 75° C., about 80° C., about 85° C., about 90° C., or about 95° C. Such MutS protein may be of thermophilic or hyperthermophilic bacterial origin. Exemplary thermostable MutS proteins include MutS proteins from *Aquifex aeolicus, Aquifex pyrophilus, Thermotoga maritima, Thermus thermophilus* and *Thermus aquaticus* (see Fukui et al., Int. J. Mol. Sci. 14:6436-6453, 2013; U.S. Pat. No. 5,877,280; Biswas and Hsieh, Journal of Biological Chemistry 271:5040-5048, 1996; and Takamatsu et al., Nucleic Acid Research 24:640-647, 1996).

In certain preferred embodiments, the MutS protein is the MutS protein from *Thermus aquaticus* (herein referred to as "Taq MutS") (GenBank Accession No. GI: 1203807, SEQ ID NO:2). In related embodiments, the MutS protein is a MutS protein with a sequence identity of at least about 30%, such as at least about 40%, about 45%, about 50%, about 55%, about 60%, about 65%, about 70%, about 75%, about 80%, about 85%, about 90%, about 95%, about 96%, about 97%, about 98%, or about 99%, with Taq MutS.

In certain preferred embodiments, the MutS protein is the MutS protein from *Thermus thermophilus* (herein referred to as "Tth MutS") (GenBank Accession No. GI: 1871501, SEQ ID NO:3). In related embodiments, the MutS protein is a MutS protein having a sequence identity of at least about 30%, such as at least about 40%, about 45%, about 50%, about 55%, about 60%, about 65%, about 70%, about 75%, about 80%, about 85%, about 90%, about 95%, about 96%, about 97%, about 98%, or about 99%, with Tth MutS.

In certain preferred embodiments, the MutS protein is the MutS protein from *Aquifex aeolicus* (herein referred to as "Aae MutS") (GenBank Accession No. GI: 2983001, SEQ ID NO:4). In related embodiments, the MutS protein is a MutS protein having a sequence identity of at least about 30%, such as at least about 40%, about 45%, about 50%, about 55%, about 60%, about 65%, about 70%, about 75%, about 80%, about 85%, about 90%, about 95%, about 96%, about 97%, about 98%, or about 99%, with Aae MutS.

In certain preferred embodiments, the MutS protein is the MutS protein from *Aquifex pyrophilus* (herein referred to as "Apy MutS") (GenBank Accession No. GI: 1619907, SEQ ID NO:5). In related embodiments, the MutS protein is a MutS protein having a sequence identity of at least about 30%, such as at least about 40%, about 45%, about 50%, about 55%, about 60%, about 65%, about 70%, about 75%, about 80%, about 85%, about 90%, about 95%, about 96%, about 97%, about 98%, or about 99%, with Apy MutS.

In certain preferred embodiments, the MutS protein is the MutS protein from *Thermotoga maritima* (herein referred to as "Tma MutS") (GenBank Accession No. GI: 1619909, SEQ ID NO:6). In related embodiments, the MutS protein is a MutS protein having a sequence identity of at least about 30%, such as at least about 40%, about 45%, about 50%, about 55%, about 60%, about 65%, about 70%, about 75%, about 80%, about 85%, about 90%, about 95%, about 96%, about 97%, about 98%, or about 99%, with Tma MutS.

For determining sequence identity, the WU-BLAST-2 program (Altschul et al., Methods in Enzymology 266:460-480, 1996) is used. This program uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. A percent sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

MutS proteins may be obtained from an organism in which they occur in nature. Alternatively, they can be produced by recombinant methods.

A MutS protein may be present in a highly multiplex single primer extension reaction at a concentration of about 0.05 to about 10 uM, such as about 0.1 to about 1 uM, or about 0.2 to about 0.5 uM.

In addition to a MutS protein, single primer extension as disclosed herein is performed in the presence of $Mg^{2+}$ at a minimum concentration of about 6 mM.

In certain embodiments, the concentration of $Mg^{2+}$ is at least about 6, at least about 7, at least about 8, at least about 9, or at least about 10 mM and/or at most about 15, at most about 16, at most about 17, at most about 18, at most about 19, at most about 20 mM, including any combination of the above-noted minimum and maximum concentrations, such as about 6 mM to about 16 mM, about 6 mM to about 20 mM, about 8 mM to about 16 mM, about 8 mM to about 20 mM, about 10 mM to about 16 mM, or about 10 mM to about 20 mM.

Single primer extension reactions disclosed herein also comprise dNTPs. Typically, dNTPs are each present at an initial concentration (i.e., concentration at the start of the reaction) of about 40 uM to about 1000 uM in the reaction mixtures.

Single primer extension reactions disclosed herein also comprise a DNA polymerase for primer extensions. Preferably, DNA polymerases are thermostable. Exemplary DNA polymerases include Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus* woesei), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*), Amplitaq Gold® DNA polymerase (Applied Biosciences), Stoffel fragment of Amplitaq® DNA Polymerase (Roche), KOD polymerase (EMD Biosciences), KOD Hot Start polymerase (EMD Biosciences), Deep Vent™ DNA polymerase (New England Biolabs), Phusion polymerase (New England Biolabs), Klentaq1 polymerase (DNA Polymerase Technology, Inc), Klentaq Long Accuracy polymerase (DNA Polymerase Technology, Inc), Omni KlenTaq™ DNA polymerase (DNA Polymerase Technology, Inc), Omni KlenTaq™ LA DNA polymerase (DNA Polymerase Technology, Inc), Platinum® Taq DNA Polymerase (Invitrogen), Hemo Klentaq™ (New England Biolabs), Platinum® Taq DNA Polymerase High Fidelity (Invitrogen), Platinum® Pfx (Invitrogen), Accuprime™ Pfx (Invitrogen), and Accuprime™ Taq DNA Polymerase High Fidelity (Invitrogen).

In embodiments where two or more primers are able to anneal to closely located regions of a target nucleic acid, the DNA polymerase preferably does not have strand displacement activity, flap endonuclease or 5'→3' exonuclease activity, with which the polymerase may destroy downstream primer extension products.

In certain preferred embodiments, the DNA polymerase does not have 3'→5" exonuclease activity.

As disclosed above, the combination of a relatively high concentration of $Mg^{2+}$ and a MutS improves primer annealing and extension specificity in a highly multiplex single primer extension reaction. In certain embodiments, the primer annealing and extension specificity is at least about 80%, about 85%, about 90% or about 95%.

The specificity of primer annealing and extension in highly multiplex single primer extension can be measured, after next generation sequencing, by the percentage of reads mapped to the targeted loci.

Also as disclosed above, the combination of a relatively high concentration of $Mg^{2+}$ and a MutS also improves primer annealing and extension efficiency in a highly multiplex primer extension reaction. In certain embodiments, the average primer annealing and extension efficiency of all of the primers other than a boosting primer (if present) in a highly multiplex single primer extension reaction is at least about 5%, about 10%, about 15%, about 20%, or about 25%.

The efficiency of primer annealing of an individual enrichment primer in a highly multiplex single primer extension reaction can be measured by measuring the number of DNA copies generated by the individual enrichment primer after primer extension, such as by a qPCR assay. For example, in certain embodiments where each enrichment primer comprises at its 5' terminus a universal sequence that is incapable of specifically annealing to a target nucleic acid, one qPCR primer can be designed to specifically anneal to the universal sequence and another qPCR primer can be designed to have a sequence identical to a portion of the target nucleic acid 5' to the region where the enrichment primer anneals. Such a qPCR assay measures the number of new DNA molecules generated by primer extension. The ratio of new DNA molecules to the input DNA amount represents the percentage of input DNA being annealed and extended by the enrichment primer.

In certain embodiments, the primer annealing and extension specificity is at least about 80%, about 85%, about 90% or about 95% and the average primer annealing and extension efficiency is at least about 5%, about 10%, about 15%, about 20%, or about 25%, including all possible combinations of the above-noted specificity and efficiency.

Products of single primer extension reactions disclosed herein may be further amplified and/or analyzed (e.g., sequenced). The further amplification may be performed using any appropriate methods known in the art.

Sequencing of extension products or amplified extension products may also be performed using any appropriate methods known in the art. In certain embodiments, high throughput sequencing platforms known in the art may be used to sequence nucleic acids prepared from single primer extension products (see, Myllykangas et al., *Bioinformatics for High Throughput Sequencing*, Rodríguez-Ezpeleta et al. (eds.), Springer Science+Business Media, LLC, 2012, pages 11-25). Exemplary high throughput DNA sequencing systems include, but are not limited to, the GS FLX sequencing system originally developed by 454 Life Sciences and later acquired by Roche (Basel, Switzerland), Genome Analyzer developed by Solexa and later acquired by Illumina Inc. (San Diego, CA) (see, Bentley, Curr Opin Genet Dev 16:545-52, 2006; Bentley et al., Nature 456:53-59, 2008), the SOLiD sequence system by Life Technologies (Foster City, CA) (see, Smith et al., Nucleic Acid Res 38: e142, 2010; Valouev et al., Genome Res 18:1051-63, 2008), CGA developed by Complete Genomics and acquired by BGI (see, Drmanac et al., Science 327:78-81, 2010), PacBio RS sequencing technology developed by Pacific Biosciences (Menlo Park, CA) (see, Eid et al., Science 323: 133-8, 2009), and Ion Torrent developed by Life Technologies Corporation (see, U.S. Patent Application Publication Nos. 2009/0026082; 2010/0137143; and 2010/0282617).

The analysis of the extension products may be used in identifying structural variations (e.g., nucleotide mutations, deletions, insertions) in target nucleic acids when compared with corresponding reference sequences. In addition, sequencing extension products from cDNA is useful in detecting fusions and splicing variants. Furthermore, comparing sequences of extension products from bisulfite treated genomic DNA with those from untreated genomic DNA may be used in determining methylation patterns of the genomic DNA.

II. Using Single Primer Extension in NGS

In a related aspect, the present disclosure provides a method for using highly multiplex single primer extension reactions described above in high throughput nucleic acid sequencing. The method comprises:

a. providing a plurality of partially double-stranded target nucleic acids each of which comprises a double-stranded target nucleic acid sequence and a single-stranded common sequence at the 5' terminus of each strand of the target nucleic acid sequence, wherein the single-stranded common sequence is the same among the plurality of the target nucleic acids;

b. providing a plurality of primers capable of specifically annealing to portions of the target nucleic acid sequences;

c. extending the primers using the target nucleic acid sequences as templates in the presence of (1) a MutS protein and (2) $Mg^{2+}$ at a minimum concentration of about 6 mM to obtain extension products; and d. sequencing the extension products or their amplification products.

The partially double-stranded target nucleic acids may be prepared from any nucleic acids of interest (e.g., genomic DNA and bisulfite-treated genomic DNA) isolated from any samples, sources, or organisms as described above in Section I.

In certain embodiments, extending the primers in step c. is performed in the presence of a boosting primer comprising the common sequence or a portion thereof that is at least about 10 nucleotides in length.

In certain embodiments, step a. comprises:

a1. fragmenting double-stranded DNA molecules to generate double-stranded DNA fragments, and a2. ligating the single-stranded common sequence to the 5' terminus of each strand of the double-stranded DNA fragment to provide the plurality of partially double-stranded nucleic acids.

Steps a1 and a2 may be performed using any appropriate methods known in the art. For example, step a2 may be performed using an adapter with the 5' portion in single-stranded formation and containing the common sequence and its 3' end portion forming a short double-stranded structure with a complementary oligonucleotide. The double-stranded 3' end can be ligated to the 5' terminus of each strand of the double-stranded DNA fragments in a regular double-strand DNA ligation reaction.

The single-stranded common sequence comprises at least about 10 nucleotides (e.g., at least about 11, 12, 13, 14, 15, 16, 17, 18, 19, or 20 nucleotides) so that a boosting primer may be designed to specifically anneal to the common sequence.

The plurality of primers in step b., single primer extensions in step c., and sequencing in step b. may be performed as described above in Section I.

In certain embodiments, the method also comprises: prior to step d., a further step of amplifying the extension products of step c. The amplification may be performed using a primer at least substantially complementary to the common sequence or a portion of the common sequence that is at least about 10 nucleotides in length and another primer capable of specifically annealing to a universal sequence at the 5' ends of the primers that have been extended in the single primer extension reaction.

An exemplary method is shown in FIG. 1. Briefly, in step 1, genomic DNA is first fragmented into smaller fragment (see step 1). In step 2, each fragment is then 5' ligated with a sequencing adapter ("NGSCounter") (an exemplary common sequence). In step 3, target-specific primers each having the same 5' universal sequence are annealed to the fragmented DNA and extended by DNA polymerase to the sequencing adapter ends. This process can be repeated multiple cycles to maximize the yield of single primer extension. An adapter primer ("boosting primer") can also be included to boost the yield of single primer extension. In step 4, the newly synthesized DNA strand, containing the 5' universal sequence and 3' adapter sequence, can be further amplified by a pair of an adapter primer (that comprises the boosting primer sequence or a portion thereof) and a universal primer (that comprises the universal sequence or a portion thereof) to prepare universal PCR library. In step 5, the library is quantified. In step 6, the nucleic acids in the library are sequenced.

III. Kits for Performing Single Primer Extensions

In another aspect, the present disclosure provides a kit for performing a highly multiplex single primer extension reaction, comprising: (1) a pool of at least 1,000 different primers, (2) a buffer concentrate comprising a MutS protein, dNTPs, and $Mg^{2+}$, wherein the concentration of $Mg^{2+}$ in a highly multiplex single primer extension reaction mixture generated from diluting the buffer concentrate is at least about 6 mM, and (3) a DNA polymerase.

The pool of primers in the kit may contain about 1,000 to about 100,000 different primers. For example, a primer pool may contain at least about 1,000, 1,500, 2,000, 2,500, 3,000, 3,500, 4,000, 4,500, or 5,000 different primers, and/or at most about 10,000, 20,000, 30,000, 40,000, 50,000, 60,000, 70,000, 80,000, 90,000, or 100,000 different primers, including any combination of the above-noted minimum and maximum numbers of different primers such as about 1,000 to about 10,000, about 1,000 to about 50,000, about 1,000 to about 100,000, about 5,000 to about 20,000, about 5,000 to about 50,000, or about 5,000 to about 100,000 different primers.

The primers in the pool may preferably be at the same concentration or a substantially similar concentration (i.e., the highest concentration of a primer is at most twice the lowest concentration of another primer).

Each primer in the pool may be about 0.01 nM to about 100 nM, preferably about 1 nM to about 40 nM, such as about 2 nM to about 20 nM.

In certain embodiments, each primer in the pool has a concentration of at least about 0.01, 0.02, 0.03, 0.04, 0.05, 0.06, 0.07, 0.08, 0.09, 0.1, 0.2, 0.3, 0.4, or 0.5 nM and/or at most about 1, 2, 3, 4, 5, 6, 7, 8, 9, 10, 11, 12, 13, 14, 15, 16, 17, 18, 19, 20, 30, 40, 50, 60, 70, 80, 90, or 100 nM, including any combination of the above-noted minimum and maximum concentrations.

The buffer concentrate in the kit comprises a MutS protein, dNTPs, and $Mg^{2+}$, wherein the concentration of $Mg^{2+}$ in a highly multiplex single primer extension reaction mixture generated from diluting the buffer concentrate is at least about 6 mM, such as about 6 mM to about 20 mM.

In certain embodiments, the concentration of $Mg^{2+}$ in a highly multiplex single primer extension reaction diluted from a buffer concentrate is at least about 6, at least about 7, at least about 8, at least about 9, or at least about 10 mM and/or at most about 15, at most about 16, at most about 17, at most about 18, at most about 19, at most about 20 mM, including any combination of the above-noted minimum and maximum concentrations, such as about 6 mM to about 16 mM, about 6 mM to about 20 mM, about 8 mM to about 16 mM, about 8 mM to about 20 mM, about 10 mM to about 16 mM, or about 10 mM to about 20 mM.

A MutS protein may be present in a highly multiplex single primer extension reaction diluted from a buffer concentrate at a concentration of about 0.05 to about 10 uM, such as about 0.1 to about 1 uM, or about 0.2 to about 0.5 uM.

dNTPs are typically each present at a concentration of about 40 to about 1000 uM in a highly multiplex single primer extension reaction diluted from a buffer concentrate.

Additional descriptions of various components of the kit, including primers, MutS proteins, dNTPs, DNA polymerases may be found above in section I.

The kit may further comprise one or more of the following additional components: a single-stranded sequence that may be ligated to the 5' terminus of each strand of double-stranded target nucleic acids as described above in Sections I and II, a boosting primer as described above in Sections I and II, a DNA ligase (e.g., T4 DNA ligase and E. coli DNA ligase), a ligation buffer, a primer pair for amplifying single primer extension products (e.g., those described above in Section II), and a sequencing primer.

In a related aspect, the present disclosure provides use of a kit disclosed herein in performing a highly multiplex primer extension reaction.

In another related aspect, the present disclosure provides use of a kit disclosed herein in nucleic acid sequencing.

EXAMPLES

Example 1

Effects of $Mg^{2+}$ Concentrations on Primer Extension Efficiency and Specificity Extension reactions of primers (each primer at a 2 nM concentration) were performed at $Mg^{2+}$ concentrations from 2 mM to 20 mM. The primer extension reaction was set up in 1× miScript buffer supplemented with various amount of $Mg^{2+}$, 2.4 U HotStatTaq, 20 nM single target specific primer with 5' universal sequence and 20 ng genomic DNA. The reaction proceeded for 20 minutes at 95° C., 15 minutes at 55° C., 15 minutes at 65° C. and 7 minutes at 72° C. Specific qPCR was used to quantify the amount of extension products.

Figure 2:
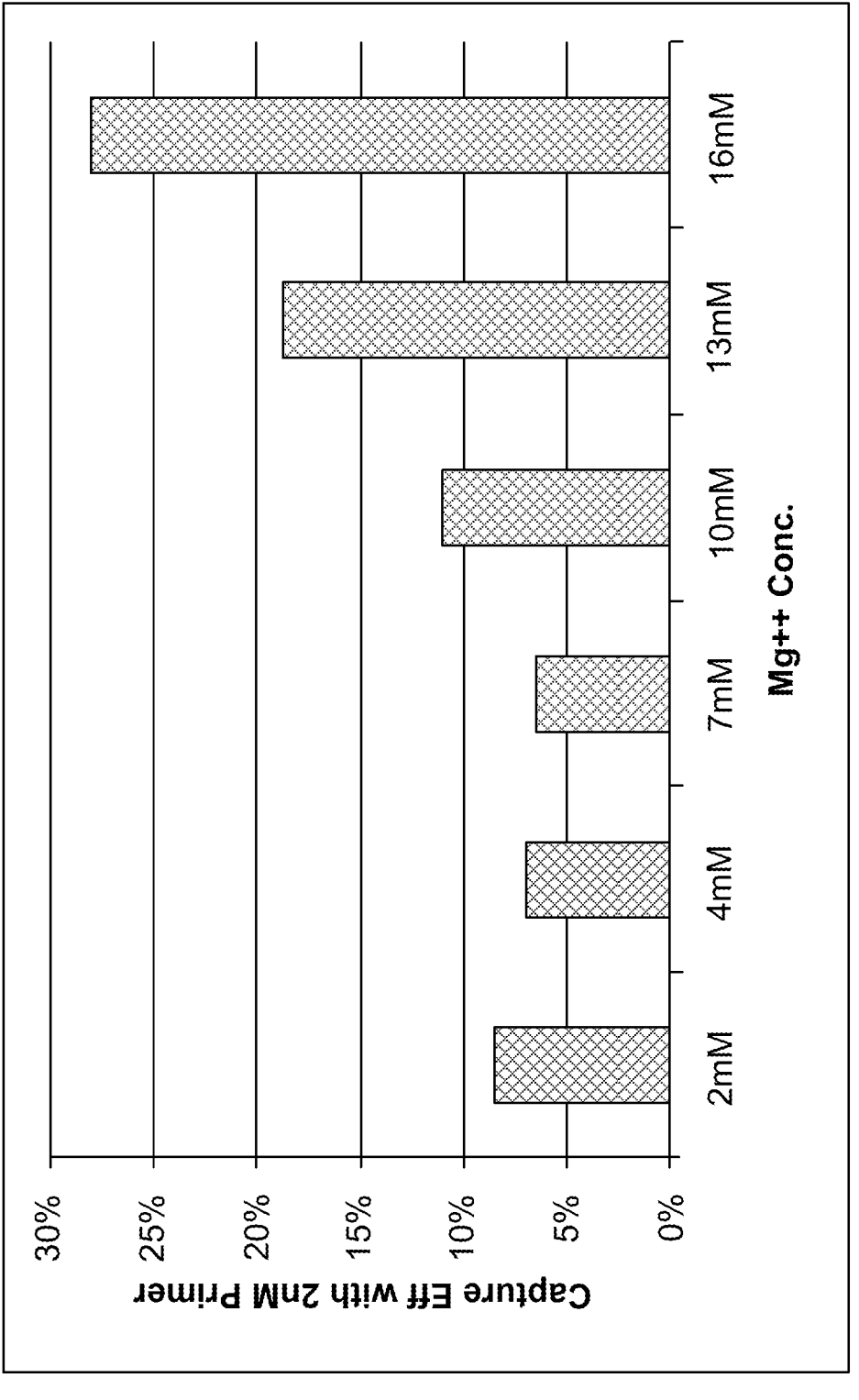
FIG. 2 is a graph showing primer annealing and extension efficiencies at various $Mg^{2+}$ concentrations.

The results (FIG. 2) show that increasing the concentration of $Mg^{2+}$ improved the primer annealing and extension efficiency.

DNA enriched using 12 mM $Mg^{2+}$ and over 1300 primers at 2 nM each and DNA enriched using 4 mM $Mg^{2+}$ and the same primers at 20 nM each were sequenced to determine primer annealing and extension specificity.

Figure 3:
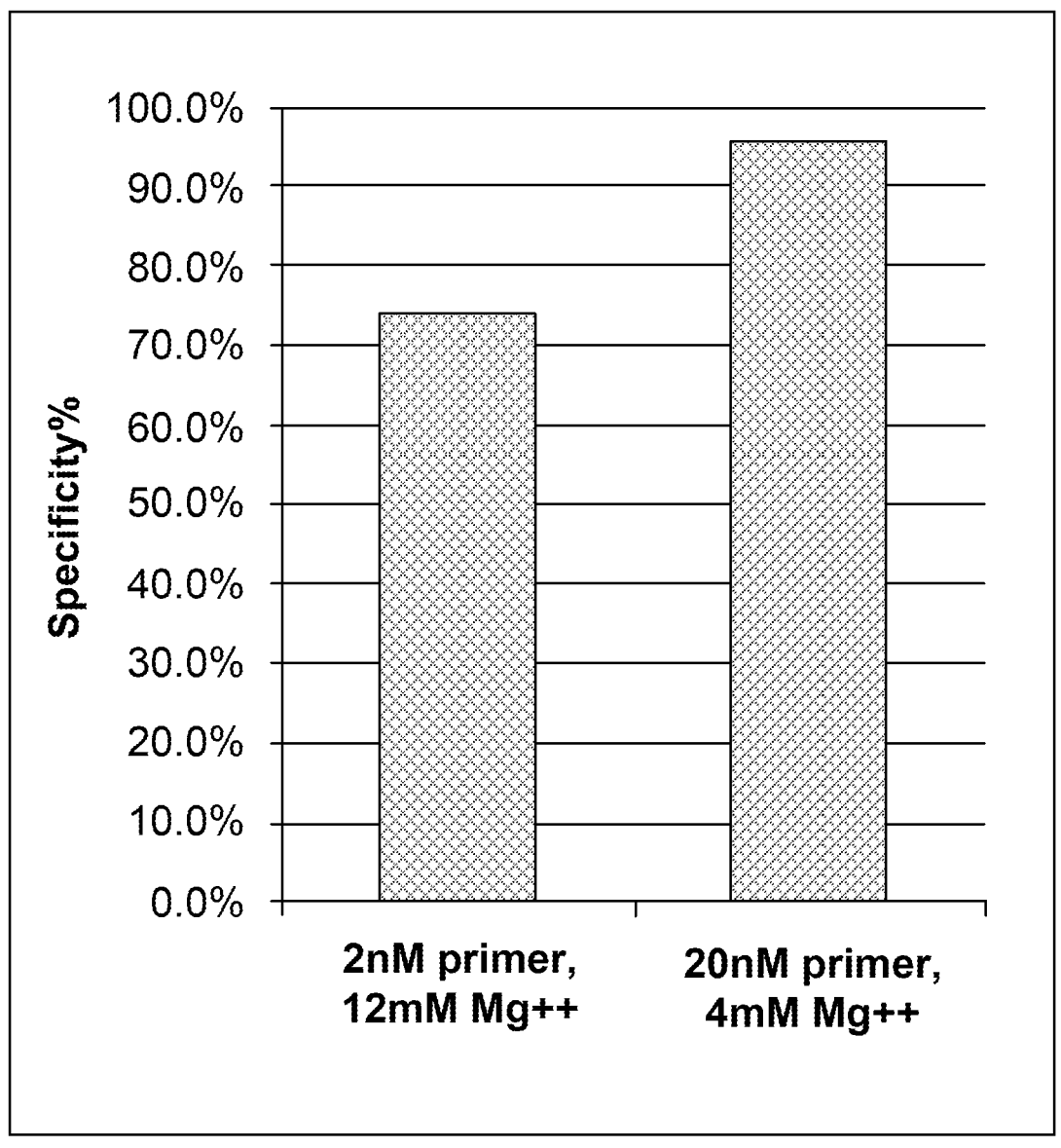
FIG. 3 is a graph comparing primer annealing and extension specificities between an extension reaction performed using 2 nM each primer and 12 mM $Mg^{2+}$ and an extension reaction performed using 20 nM each primer and 4 mM $Mg^{2+}$.

The results (FIG. 3) show that the higher $Mg^{2+}$ concentration significantly reduced the specificity of primer annealing. While not wishing to be bound by any particular theory, the present inventors believe that under higher $Mg^{2+}$ concentrations, non-specific binding of primers to DNA templates was stabilized along with increased specific annealing.

Example 2

Effects of MutS on Specificity of Primer Extensions Performed at Relatively High $Mg^{2+}$ Concentrations This example demonstrates that MutS improved specificity of highly multiplex targeted enrichment performed at a relatively high $Mg^{2+}$ concentration.

Methods

Fragmenting gDNA (Sonication Method)

1 ug genomic DNA (gDNA) was diluted in 100 ul elution buffer and sonicated on BIORUPTOR300 (power level low, 10 cycles of 30 seconds on and 30 seconds off). The resulting DNA fragments were purified using QIAGEN's MinElute Column.

Library Construction

A sequencing library was prepared using the above-generated gDNA fragments according to the End Repair, A-Addition, Adapter Ligation and Clean up and Size Selection of DNA protocols as described in QIAGEN GeneRead Library Prep for Illumina Kit. The library was quantified and diluted to 20 ng/ul.

Primer Extension

The primer extension reactions were set up as follows:

| Primer Extension | 20 nM Primer Setup Volume (ul) | 2 nM Primer setup Volume (ul) |
| --- | --- | --- |
| GeneRead V2 buffer (5×) | 8 | 8 |
| dNTP (2 mM each) | 4 | 4 |
| DNA library (from previous step, 20 ng/ul) | 1 | 1 |

-continued

| | 20 nM Primer Setup | | 2 nM Primer setup | |
|---|---|---|---|---|
| Primer Extension | Volume (ul) | | Volume (ul) | |
| Taq | 1.6 | | 1.6 | |
| SPE Primer pool (76 nM) | 10.5 | 20 nM final | 1.05 | 2 nM final |
| Ilumina_F primer (10 uM) | 1.6 | | 1.6 | |
| MgCl₂ (80 mM) | 0 | | 4 | |
| Taq MutS | 0 | | 3 | |
| H₂O | 13.3 | | 15.75 | |
| Total | 40 | | 40 | |

The final $Mg^{2+}$ concentrations of 20 nM primer setup and 2 nM primer setup were 4 and 12 mM, respectively.

Primer extension reactions were performed in a thermal cycler as follows: 95° C. for 15 minutes, 5 cycles of 95° C. for 15 seconds and 68° C. for 10 minutes, 72° C. for 5 minutes, and 4° C. hold.

60 ul $H_2O$ was added to each of the primer extension mixtures to bring the volume to 100 ul. The extension products were purified by 2 rounds Ampure beads purification (1.2× beads ratio) and eluted in 15 ul Buffer EB.

Universal PCR

Primer extension products were further amplified in a universal PCR reaction as follows:

| Universal qPCR | Volume (ul) |
|---|---|
| GeneRead V2 buffer (5×) | 5 |
| dNTP (2 mM each) | 2.5 |
| Template (from previous step) | 11.5 |
| Taq | 1 |
| Universal primer (IL2) (4 uM) | 2.5 |
| IL1_ID(#)-RS2 primer (4 uM) | 2.5 |
| Total | 25 |

The reaction was performed in a thermal cycler as follows: 95° C. for 15 minutes, 26 cycles of 95° C. for 15 seconds and 65° C. for 2 minutes, and 4° C. hold.

The amplification products were purified via one round Ampure beads purification (1.2× beads ratio) and eluted in 20 ul buffer EB. 5 ul of the purified amplification products were checked with a 1.2% Agarose gel.

Library Quantification and Sequencing

Quantification of the amplified library and sequencing were performed according to the manufacturer's instructions.

Results

Figure 4:
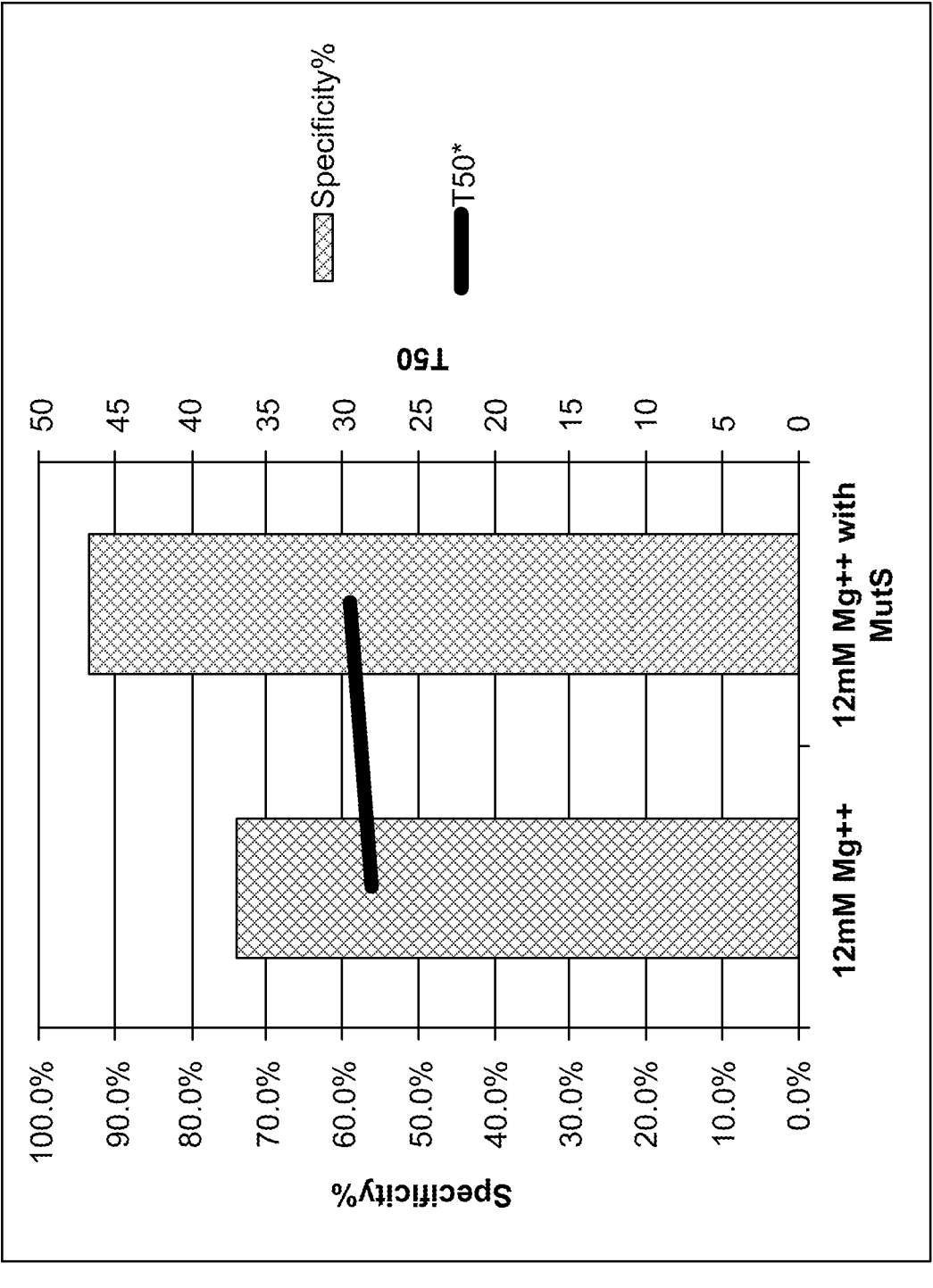
FIG. 4 is a graph comparing primer annealing and extension specificities and uniformities (T50) between an extension reaction performed at 12 mM $Mg^{2+}$ without MutS and an extension reaction performed at 12 mM $Mg^{2+}$ with MutS.

The results (FIG. 4) show that adding Taq MutS in primer extension reactions together with 12 mM $Mg^{2+}$ significantly improve primer annealing and extension specificity at no cost of primer annealing and extension efficiency as indicated by consistently good sequence uniformity.

T50 is an indicator of sequence uniformity. It is defined as the percentage of total sequence throughput used by regions sequenced at below 50% of the mean read depth of all target regions. In a perfect uniform scenario, the T50 value is 50.

While not wishing to be bound by any particular theory, the present inventors hypothesize that non-specific primer-template hybrids formed during primer extension performed at a high $Mg^{2+}$ concentration presumably contain mismatches and bulges in the middle of the primer sequences, but perfectly anneal at the 3' termini of the primers so that DNA polymerase can extend from such termini. MutS specifically binds to those bulges created by sequence mismatches and thus block a DNA polymerase from binding to and extending the non-specific primer-template duplex. The specific primer-template duplex would have complementary sequences and no bulge in the structure so that MutS would not bind tightly. Thus, extension of primers that specifically bind to their templates will not be affected.

The various embodiments described above can be combined to provide further embodiments. All of the U.S. patents, U.S. patent application publications, U.S. patent applications, foreign patents, foreign patent applications and non-patent publications referred to in this specification and/ or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for performing a multiplex single primer extension reaction, comprising:

(a) extending a plurality of different primers in a single primer extension reaction using a plurality of different double-stranded or partially double-stranded target nucleic acids as templates in a reaction mixture that comprises (1) a MutS protein and (2) $Mg^{2+}$ at a minimum concentration of about 6 mM to generate extension products, wherein the plurality of different primers differs from each other, the plurality of different primers anneals to only one strand of the different double-stranded or partially double-stranded target nucleic acids, and the reaction mixture does not comprise a primer that anneals to the other strand of the different double-stranded or partially double-stranded target nucleic acids to exponentially amplify one or more of the different double-stranded or partially double-stranded target nucleic acids or a portion thereof except where most or all of the double-stranded or partially double-stranded target nucleic acids comprise a common sequence at least 10 nucleotides in length, a boosting primer comprising the common sequence or a portion thereof that is at least 10 nucleotides in length that anneals to a sequence complementary to the common sequence or a portion thereof in the other strand of the different double-stranded or partially double-stranded target nucleic acids is optionally present.

2. The method of claim 1, wherein the single primer extension reaction is performed in the absence of the boosting primer.

3. The method of claim 1, wherein most or all of the target nucleic acids comprise the common sequence at least 10 nucleotides in length, and wherein the reaction is performed in the presence of the boosting primer that comprises the common sequence or a portion thereof that is at least 10 nucleotides in length and anneals to the sequence complementary to the common sequence or a portion thereof in the other strand of the different double-stranded or partially double-stranded target nucleic acids.

4. The method of claim 1, wherein each of the different primers is present in the single primer extension reaction at a concentration of no more than 20 nM.

5. The method of claim 3, wherein each of the primers other than the boosting primer is present in the single primer extension reaction at a concentration of 1 nM to 10 nM.

6. The method of claim 1, wherein $Mg^{2+}$ is present in the single primer extension reaction at a concentration of 6 mM to 20 mM.

7. The method of claim 1, wherein the plurality of target nucleic acids are genomic DNA or amplification products of genomic DNA.

8. The method of claim 1, wherein the plurality of target nucleic acids are cDNA or amplification products of cDNA.

9. The method of claim 1, wherein the plurality of target nucleic acids are bisulfite treated genomic DNA or its amplified products.

10. The method of claim 1, wherein the MutS protein is a *Thermus aquaticus* MutS protein.

11. The method of claim 1, wherein the primer annealing and extension specificity of the single primer extension reaction is at least 80%.

12. The method of claim 1, wherein the average primer annealing and extension efficiency of the single primer extension reaction is at least 10%.

13. The method of claim 1, further comprising:

(b) amplifying the extension product(s) to generate amplified extension product(s), and (c) sequencing the extension product(s) or the amplified extension products.

14. The method of claim 1, wherein the target nucleic acids are partially double-stranded, and comprise a double-stranded target nucleic acid sequence and a single-stranded common sequence at the 5' terminus of each strand of the target nucleic acid sequence, wherein the single-stranded common sequence is at least 10 nucleotides in length.

15. The method of claim 14, wherein the target nucleic acids are DNA molecules, the method comprising: prior to step (a), (i) fragmenting the DNA molecules to generate double-stranded DNA fragments, and (ii) ligating the single-stranded common sequence to the 5' terminus of each strand of the double-stranded DNA fragment to provide partially double-stranded target nucleic acids.

16. The method of claim 1, wherein each of the different primers comprises at its 5' terminus a universal sequence that is incapable of specifically annealing to a region of a target nucleic acid.

17. The method of claim 1, wherein step (a) is performed in the presence of a high fidelity DNA polymerase.

18. The method of claim 17, wherein the high fidelity DNA polymerase is KOD polymerase or Pfu polymerase.

19. The method of claim 3, wherein step (a) comprises performing a PCR reaction.

* * * * *

```
                    SEQUENCE LISTING

<160> NUMBER OF SEQ ID NOS: 6

<210> SEQ ID NO 1
<211> LENGTH: 853
<212> TYPE: PRT
<213> ORGANISM: Escherichia coli

<400> SEQUENCE: 1

Met Ser Ala Ile Glu Asn Phe Asp Ala His Thr Pro Met Met Gln Gln
1               5                   10                  15

Tyr Leu Arg Leu Lys Ala Gln His Pro Glu Ile Leu Leu Phe Tyr Arg
            20                  25                  30

Met Gly Asp Phe Tyr Glu Leu Phe Tyr Asp Asp Ala Lys Arg Ala Ser
        35                  40                  45

Gln Leu Leu Asp Ile Ser Leu Thr Lys Arg Gly Ala Ser Ala Gly Glu
```

-continued

```
            50                  55                  60

Pro Ile Pro Met Ala Gly Ile Pro Tyr His Ala Val Glu Asn Tyr Leu
65                  70                  75                  80

Ala Lys Leu Val Asn Gln Gly Glu Ser Val Ala Ile Cys Glu Gln Ile
                85                  90                  95

Gly Asp Pro Ala Thr Ser Lys Gly Pro Val Glu Arg Lys Val Val Arg
            100                 105                 110

Ile Val Thr Pro Gly Thr Ile Ser Asp Glu Ala Leu Leu Gln Glu Arg
            115                 120                 125

Gln Asp Asn Leu Leu Ala Ala Ile Trp Gln Asp Ser Lys Gly Phe Gly
        130                 135                 140

Tyr Ala Thr Leu Asp Ile Ser Ser Gly Arg Phe Arg Leu Ser Glu Pro
145                 150                 155                 160

Ala Asp Arg Glu Thr Met Ala Ala Glu Leu Gln Arg Thr Asn Pro Ala
            165                 170                 175

Glu Leu Leu Tyr Ala Glu Asp Phe Ala Glu Met Ser Leu Ile Glu Gly
            180                 185                 190

Arg Arg Gly Leu Arg Arg Arg Pro Leu Trp Glu Phe Glu Ile Asp Thr
        195                 200                 205

Ala Arg Gln Gln Leu Asn Leu Gln Phe Gly Thr Arg Asp Leu Val Gly
        210                 215                 220

Phe Gly Val Glu Asn Ala Pro Arg Gly Leu Cys Ala Ala Gly Cys Leu
225                 230                 235                 240

Leu Gln Tyr Ala Lys Asp Thr Gln Arg Thr Thr Leu Pro His Ile Arg
            245                 250                 255

Ser Ile Thr Met Glu Arg Glu Gln Asp Ser Ile Ile Met Asp Ala Ala
            260                 265                 270

Thr Arg Arg Asn Leu Glu Ile Thr Gln Asn Leu Ala Gly Gly Ala Glu
        275                 280                 285

Asn Thr Leu Ala Ser Val Leu Asp Cys Thr Val Thr Pro Met Gly Ser
        290                 295                 300

Arg Met Leu Lys Arg Trp Leu His Met Pro Val Arg Asp Thr Arg Val
305                 310                 315                 320

Leu Leu Glu Arg Gln Gln Thr Ile Gly Ala Leu Gln Asp Phe Thr Ala
            325                 330                 335

Gly Leu Gln Pro Val Leu Arg Gln Val Gly Asp Leu Glu Arg Ile Leu
            340                 345                 350

Ala Arg Leu Ala Leu Arg Thr Ala Arg Pro Arg Asp Leu Ala Arg Met
        355                 360                 365

Arg His Ala Phe Gln Gln Leu Pro Glu Leu Arg Ala Gln Leu Glu Thr
        370                 375                 380

Val Asp Ser Ala Pro Val Gln Ala Leu Arg Glu Lys Met Gly Glu Phe
385                 390                 395                 400

Ala Glu Leu Arg Asp Leu Leu Glu Arg Ala Ile Ile Asp Thr Pro Pro
            405                 410                 415

Val Leu Val Arg Asp Gly Gly Val Ile Ala Ser Gly Tyr Asn Glu Glu
            420                 425                 430

Leu Asp Glu Trp Arg Ala Leu Ala Asp Gly Ala Thr Asp Tyr Leu Glu
        435                 440                 445

Arg Leu Glu Val Arg Glu Arg Glu Arg Thr Gly Leu Asp Thr Leu Lys
        450                 455                 460

Val Gly Phe Asn Ala Val His Gly Tyr Tyr Ile Gln Ile Ser Arg Gly
465                 470                 475                 480
```

-continued

```
Gln Ser His Leu Ala Pro Ile Asn Tyr Met Arg Arg Gln Thr Leu Lys
            485             490             495

Asn Ala Glu Arg Tyr Ile Ile Pro Glu Leu Lys Glu Tyr Glu Asp Lys
            500             505             510

Val Leu Thr Ser Lys Gly Lys Ala Leu Ala Leu Glu Lys Gln Leu Tyr
            515             520             525

Glu Glu Leu Phe Asp Leu Leu Leu Pro His Leu Glu Ala Leu Gln Gln
        530             535             540

Ser Ala Ser Ala Leu Ala Glu Leu Asp Val Leu Val Asn Leu Ala Glu
545             550             555             560

Arg Ala Tyr Thr Leu Asn Tyr Thr Cys Pro Thr Phe Ile Asp Lys Pro
            565             570             575

Gly Ile Arg Ile Thr Glu Gly Arg His Pro Val Val Glu Gln Val Leu
            580             585             590

Asn Glu Pro Phe Ile Ala Asn Pro Leu Asn Leu Ser Pro Gln Arg Arg
            595             600             605

Met Leu Ile Ile Thr Gly Pro Asn Met Gly Gly Lys Ser Thr Tyr Met
        610             615             620

Arg Gln Thr Ala Leu Ile Ala Leu Met Ala Tyr Ile Gly Ser Tyr Val
625             630             635             640

Pro Ala Gln Lys Val Glu Ile Gly Pro Ile Asp Arg Ile Phe Thr Arg
            645             650             655

Val Gly Ala Ala Asp Asp Leu Ala Ser Gly Arg Ser Thr Phe Met Val
            660             665             670

Glu Met Thr Glu Thr Ala Asn Ile Leu His Asn Ala Thr Glu Tyr Ser
            675             680             685

Leu Val Leu Met Asp Glu Ile Gly Arg Gly Thr Ser Thr Tyr Asp Gly
        690             695             700

Leu Ser Leu Ala Trp Ala Cys Ala Glu Asn Leu Ala Asn Lys Ile Lys
705             710             715             720

Ala Leu Thr Leu Phe Ala Thr His Tyr Phe Glu Leu Thr Gln Leu Pro
            725             730             735

Glu Lys Met Glu Gly Val Ala Asn Val His Leu Asp Ala Leu Glu His
            740             745             750

Gly Asp Thr Ile Ala Phe Met His Ser Val Gln Asp Gly Ala Ala Ser
            755             760             765

Lys Ser Tyr Gly Leu Ala Val Ala Ala Leu Ala Gly Val Pro Lys Glu
            770             775             780

Val Ile Lys Arg Ala Arg Gln Lys Leu Arg Glu Leu Glu Ser Ile Ser
785             790             795             800

Pro Asn Ala Ala Ala Thr Gln Val Asp Gly Thr Gln Met Ser Leu Leu
            805             810             815

Ser Val Pro Glu Glu Thr Ser Pro Ala Val Glu Ala Leu Glu Asn Leu
            820             825             830

Asp Pro Asp Ser Leu Thr Pro Arg Gln Ala Leu Glu Trp Ile Tyr Arg
            835             840             845

Leu Lys Ser Leu Val
    850
```

```
<210> SEQ ID NO 2
<211> LENGTH: 811
<212> TYPE: PRT
<213> ORGANISM: Thermus aquaticus
```

<400> SEQUENCE: 2

```
Met Glu Gly Met Leu Lys Gly Glu Gly Pro Gly Pro Leu Pro Pro Leu
1               5                   10                  15

Leu Gln Gln Tyr Val Glu Leu Arg Asp Gln Tyr Pro Asp Tyr Leu Leu
                20                  25                  30

Leu Phe Gln Val Gly Asp Phe Tyr Glu Cys Phe Gly Glu Asp Ala Glu
            35                  40                  45

Arg Leu Ala Arg Ala Leu Gly Leu Val Leu Thr His Lys Thr Ser Lys
    50                  55                  60

Asp Phe Thr Thr Pro Met Ala Gly Ile Pro Leu Arg Ala Phe Glu Ala
65                  70                  75                  80

Tyr Ala Glu Arg Leu Leu Lys Met Gly Phe Arg Leu Ala Val Ala Asp
                85                  90                  95

Gln Val Glu Pro Ala Glu Glu Ala Glu Gly Leu Val Arg Arg Glu Val
                100                 105                 110

Thr Gln Leu Leu Thr Pro Gly Thr Leu Leu Gln Glu Ser Leu Leu Pro
            115                 120                 125

Arg Glu Ala Asn Tyr Leu Ala Ala Ile Ala Thr Gly Asp Gly Trp Gly
    130                 135                 140

Leu Ala Phe Leu Asp Val Ser Thr Gly Glu Phe Lys Gly Thr Val Leu
145                 150                 155                 160

Lys Ser Lys Ser Ala Leu Tyr Asp Glu Leu Phe Arg His Arg Pro Ala
                165                 170                 175

Glu Val Leu Leu Ala Pro Glu Leu Leu Glu Asn Gly Ala Phe Leu Asp
            180                 185                 190

Glu Phe Arg Lys Arg Phe Pro Val Met Leu Ser Glu Ala Pro Phe Glu
            195                 200                 205

Pro Glu Gly Glu Gly Pro Leu Ala Leu Arg Arg Ala Arg Gly Ala Leu
    210                 215                 220

Leu Ala Tyr Ala Gln Arg Thr Gln Gly Gly Ala Leu Ser Leu Gln Pro
225                 230                 235                 240

Phe Arg Phe Tyr Asp Pro Gly Ala Phe Met Arg Leu Pro Glu Ala Thr
            245                 250                 255

Leu Arg Ala Leu Glu Val Phe Glu Pro Leu Arg Gly Gln Asp Thr Leu
            260                 265                 270

Phe Ser Val Leu Asp Glu Thr Arg Thr Ala Pro Gly Arg Arg Leu Leu
            275                 280                 285

Gln Ser Trp Leu Arg His Pro Leu Leu Asp Arg Gly Pro Leu Glu Ala
    290                 295                 300

Arg Leu Asp Arg Val Glu Gly Phe Val Arg Glu Gly Ala Leu Arg Glu
305                 310                 315                 320

Gly Val Arg Arg Leu Leu Tyr Arg Leu Ala Asp Leu Glu Arg Leu Ala
                325                 330                 335

Thr Arg Leu Glu Leu Gly Arg Ala Ser Pro Lys Asp Leu Gly Ala Leu
            340                 345                 350

Arg Arg Ser Leu Gln Ile Leu Pro Glu Leu Arg Ala Leu Leu Gly Glu
            355                 360                 365

Glu Val Gly Leu Pro Asp Leu Ser Pro Leu Lys Glu Glu Leu Glu Ala
    370                 375                 380

Ala Leu Val Glu Asp Pro Pro Leu Lys Val Ser Glu Gly Gly Leu Ile
385                 390                 395                 400

Arg Glu Gly Tyr Asp Pro Asp Leu Asp Ala Leu Arg Ala Ala His Arg
                405                 410                 415
```

-continued

```
Glu Gly Val Ala Tyr Phe Leu Glu Leu Glu Glu Arg Glu Arg Glu Arg
            420                 425                 430

Thr Gly Ile Pro Thr Leu Lys Val Gly Tyr Asn Ala Val Phe Gly Tyr
            435                 440                 445

Tyr Leu Glu Val Thr Arg Pro Tyr Tyr Glu Arg Val Pro Lys Glu Tyr
            450                 455                 460

Arg Pro Val Gln Thr Leu Lys Asp Arg Gln Arg Tyr Thr Leu Pro Glu
465                 470                 475                 480

Met Lys Glu Lys Glu Arg Glu Val Tyr Arg Leu Glu Ala Leu Ile Arg
                485                 490                 495

Arg Arg Glu Glu Glu Val Phe Leu Glu Val Arg Glu Arg Ala Lys Arg
                500                 505                 510

Gln Ala Glu Ala Leu Arg Glu Ala Ala Arg Ile Leu Ala Glu Leu Asp
            515                 520                 525

Val Tyr Ala Ala Leu Ala Glu Val Ala Val Arg Tyr Gly Tyr Val Arg
            530                 535                 540

Pro Arg Phe Gly Asp Arg Leu Gln Ile Arg Ala Gly Arg His Pro Val
545                 550                 555                 560

Val Glu Arg Arg Thr Glu Phe Val Pro Asn Asp Leu Glu Met Ala His
                565                 570                 575

Glu Leu Val Leu Ile Thr Gly Pro Asn Met Ala Gly Lys Ser Thr Phe
                580                 585                 590

Leu Arg Gln Thr Ala Leu Ile Ala Leu Leu Ala Gln Val Gly Ser Phe
                595                 600                 605

Val Pro Ala Glu Glu Ala His Leu Pro Leu Phe Asp Gly Ile Tyr Thr
            610                 615                 620

Arg Ile Gly Ala Ser Asp Asp Leu Ala Gly Gly Lys Ser Thr Phe Met
625                 630                 635                 640

Val Glu Met Glu Glu Val Ala Leu Ile Leu Lys Glu Ala Thr Glu Asn
                645                 650                 655

Ser Leu Val Leu Leu Asp Glu Val Gly Arg Gly Thr Ser Ser Leu Asp
                660                 665                 670

Gly Val Ala Ile Ala Thr Ala Val Ala Glu Ala Leu His Glu Arg Arg
            675                 680                 685

Ala Tyr Thr Leu Phe Ala Thr His Tyr Phe Glu Leu Thr Ala Leu Gly
            690                 695                 700

Leu Pro Arg Leu Lys Asn Leu His Val Ala Ala Arg Glu Glu Ala Gly
705                 710                 715                 720

Gly Leu Val Phe Tyr His Gln Val Leu Pro Gly Pro Ala Ser Lys Ser
                725                 730                 735

Tyr Gly Val Glu Val Ala Ala Met Ala Gly Leu Pro Lys Glu Val Val
                740                 745                 750

Ala Arg Ala Arg Ala Leu Leu Gln Ala Met Ala Ala Arg Arg Glu Gly
            755                 760                 765

Ala Leu Asp Ala Val Leu Glu Arg Leu Leu Ala Leu Asp Pro Asp Arg
            770                 775                 780

Leu Thr Pro Leu Glu Ala Leu Arg Leu Leu Gln Glu Leu Lys Ala Leu
785                 790                 795                 800

Ala Leu Gly Ala Pro Leu Asp Thr Met Lys Gly
                805                 810
```

```
<210> SEQ ID NO 3
<211> LENGTH: 819
```

```
<212> TYPE: PRT
<213> ORGANISM: Thermus thermophilus

<400> SEQUENCE: 3

Met Gly Gly Tyr Gly Gly Val Lys Met Glu Gly Met Leu Lys Gly Glu
1               5                   10                  15

Gly Pro Gly Pro Leu Pro Pro Leu Leu Gln Gln Tyr Val Glu Leu Arg
                20                  25                  30

Asp Arg Tyr Pro Asp Tyr Leu Leu Leu Phe Gln Val Gly Asp Phe Tyr
            35                  40                  45

Glu Cys Phe Gly Glu Asp Ala Glu Arg Leu Ala Arg Ala Leu Gly Leu
        50                  55                  60

Val Leu Thr His Lys Thr Ser Lys Asp Phe Thr Thr Pro Met Ala Gly
65                  70                  75                  80

Ile Pro Ile Arg Ala Phe Asp Ala Tyr Ala Glu Arg Leu Leu Lys Met
                85                  90                  95

Gly Phe Arg Leu Ala Val Ala Asp Gln Val Glu Pro Ala Glu Glu Ala
            100                 105                 110

Glu Gly Leu Val Arg Arg Glu Val Thr Gln Leu Leu Thr Pro Gly Thr
        115                 120                 125

Leu Thr Gln Glu Ala Leu Leu Pro Arg Glu Ala Asn Tyr Leu Ala Ala
    130                 135                 140

Ile Ala Thr Gly Asp Gly Trp Gly Leu Ala Phe Leu Asp Val Ser Thr
145                 150                 155                 160

Gly Glu Phe Lys Gly Thr Leu Leu Lys Ser Lys Ser Ala Leu Tyr Asp
                165                 170                 175

Glu Leu Phe Arg His Arg Pro Ala Glu Val Leu Leu Ala Pro Glu Leu
            180                 185                 190

Arg Glu Asn Glu Ala Phe Val Ala Glu Phe Arg Lys Arg Phe Pro Val
        195                 200                 205

Met Leu Ser Glu Ala Pro Phe Glu Pro Gln Gly Glu Gly Pro Leu Ala
    210                 215                 220

Leu Arg Arg Ala Gln Gly Ala Leu Leu Ala Tyr Ala Arg Ala Thr Gln
225                 230                 235                 240

Gly Gly Ala Leu Ser Val Arg Pro Phe Arg Leu Tyr Asp Pro Gly Ala
                245                 250                 255

Phe Val Arg Leu Pro Glu Ala Ser Leu Lys Ala Leu Glu Val Phe Glu
            260                 265                 270

Pro Leu Arg Gly Gln Asp Thr Leu Phe Gly Val Leu Asp Glu Thr Arg
        275                 280                 285

Thr Ala Pro Gly Arg Arg Leu Leu Gln Ala Trp Leu Arg His Pro Leu
    290                 295                 300

Leu Glu Arg Gly Pro Leu Glu Ala Arg Leu Asp Arg Val Glu Arg Phe
305                 310                 315                 320

Val Arg Glu Gly Ala Leu Arg Glu Gly Val Arg Arg Leu Leu Phe Arg
                325                 330                 335

Leu Ala Asp Leu Glu Arg Leu Ala Thr Arg Leu Glu Leu Ser Arg Ala
            340                 345                 350

Ser Pro Arg Asp Leu Ala Ala Leu Arg Arg Ser Leu Glu Ile Leu Pro
        355                 360                 365

Glu Leu Lys Gly Leu Leu Gly Glu Glu Val Gly Leu Pro Asp Leu Ser
    370                 375                 380

Gly Leu Leu Glu Glu Leu Arg Ala Ala Leu Val Glu Asp Pro Pro Leu
385                 390                 395                 400
```

-continued

```
Lys Val Ser Glu Gly Gly Leu Ile Arg Glu Gly Tyr Asp Pro Asp Leu
            405             410             415

Asp Ala Leu Arg Arg Ala His Ala Glu Gly Val Ala Tyr Phe Leu Asp
            420             425             430

Leu Glu Ala Arg Glu Lys Glu Arg Thr Gly Ile Pro Thr Leu Lys Val
            435             440             445

Gly Tyr Asn Ala Val Phe Gly Tyr Tyr Leu Glu Val Thr Arg Pro Tyr
    450             455             460

Tyr Glu Lys Val Pro Gln Glu Tyr Arg Pro Val Gln Thr Leu Lys Asp
465             470             475             480

Arg Gln Arg Tyr Thr Leu Pro Glu Met Lys Glu Arg Glu Arg Glu Leu
            485             490             495

Tyr Arg Leu Glu Ala Leu Ile Lys Arg Arg Glu Glu Glu Val Phe Leu
            500             505             510

Ala Leu Arg Glu Arg Ala Arg Lys Glu Ala Glu Ala Leu Arg Glu Ala
            515             520             525

Ala Arg Ile Leu Ala Glu Leu Asp Val Tyr Ala Ala Leu Ala Glu Val
    530             535             540

Ala Val Arg His Gly Tyr Thr Arg Pro Arg Phe Gly Glu Arg Leu Arg
545             550             555             560

Ile Arg Ala Gly Arg His Pro Val Val Glu Arg Arg Thr Ala Phe Val
            565             570             575

Pro Asn Asp Leu Glu Met Ala His Glu Leu Val Leu Val Thr Gly Pro
            580             585             590

Asn Met Ala Gly Lys Ser Thr Phe Leu Arg Gln Thr Ala Leu Ile Ala
    595             600             605

Leu Leu Ala Gln Ile Gly Ser Phe Val Pro Ala Glu Glu Ala Glu Leu
    610             615             620

Pro Leu Phe Asp Gly Ile Tyr Thr Arg Ile Gly Ala Ser Asp Asp Leu
625             630             635             640

Ala Gly Gly Lys Ser Thr Phe Met Val Glu Met Glu Glu Val Ala Leu
            645             650             655

Val Leu Lys Glu Ala Thr Glu Arg Ser Leu Val Leu Leu Asp Glu Val
            660             665             670

Gly Arg Gly Thr Ser Ser Leu Asp Gly Val Ala Ile Ala Thr Ala Leu
    675             680             685

Ala Glu Ala Leu His Glu Arg Arg Cys Tyr Thr Leu Phe Ala Thr His
    690             695             700

Tyr Phe Glu Leu Thr Ala Leu Ala Leu Pro Arg Leu Lys Asn Leu His
705             710             715             720

Val Ala Ala Lys Glu Glu Glu Gly Gly Leu Val Phe Tyr His Gln Val
            725             730             735

Leu Pro Gly Pro Ala Ser Lys Ser Tyr Gly Val Glu Val Ala Glu Met
            740             745             750

Ala Gly Leu Pro Lys Glu Val Val Glu Arg Ala Arg Ala Leu Leu Ser
    755             760             765

Ala Met Ala Ala Arg Arg Glu Gly Ala Leu Glu Glu Val Leu Glu Arg
    770             775             780

Leu Leu Ala Leu Asp Pro Asp Arg Leu Thr Pro Leu Glu Ala Leu Arg
785             790             795             800

Phe Leu His Glu Leu Lys Ala Leu Ala Leu Gly Leu Pro Leu Gly Ser
            805             810             815
```

-continued

Met Lys Gly

<210> SEQ ID NO 4
<211> LENGTH: 859
<212> TYPE: PRT
<213> ORGANISM: Aquifex aeolicus

<400> SEQUENCE: 4

Met Glu Lys Ser Glu Lys Glu Leu Thr Pro Met Leu Ser Gln Tyr His
1               5                   10                  15

Tyr Phe Lys Asn Gln Tyr Pro Asp Cys Leu Leu Leu Phe Arg Leu Gly
            20                  25                  30

Asp Phe Tyr Glu Leu Phe Tyr Glu Asp Ala Tyr Ile Gly Ser Lys Glu
            35                  40                  45

Leu Gly Leu Val Leu Thr Ser Arg Pro Ala Gly Lys Gly Lys Glu Arg
        50                  55                  60

Ile Pro Met Cys Gly Val Pro Tyr His Ser Ala Asn Ser Tyr Ile Ala
65                  70                  75                  80

Lys Leu Val Asn Lys Gly Tyr Lys Val Ala Ile Cys Glu Gln Val Glu
                85                  90                  95

Asp Pro Ser Lys Ala Lys Gly Ile Val Lys Arg Glu Val Val Arg Val
            100                 105                 110

Ile Thr Pro Gly Thr Phe Phe Glu Arg Asp Thr Gly Gly Leu Ala Ser
            115                 120                 125

Leu Tyr Lys Lys Gly Asn His Tyr Tyr Val Gly Tyr Leu Asn Leu Ala
        130                 135                 140

Val Gly Glu Phe Leu Gly Ala Lys Val Lys Ile Glu Glu Leu Leu Asp
145                 150                 155                 160

Leu Leu Ser Lys Leu Asn Ile Lys Glu Ile Leu Val Lys Lys Gly Glu
                165                 170                 175

Lys Leu Pro Glu Glu Leu Glu Lys Val Leu Lys Val Tyr Val Ser Glu
            180                 185                 190

Leu Glu Glu Glu Phe Phe Glu Glu Gly Ser Glu Glu Ile Leu Lys Asp
        195                 200                 205

Phe Gly Val Leu Ser Leu Gln Ala Phe Gly Phe Glu Glu Asp Thr Tyr
    210                 215                 220

Ser Leu Pro Leu Gly Ala Val Tyr Lys Tyr Ala Lys Thr Thr Gln Lys
225                 230                 235                 240

Gly Tyr Thr Pro Leu Ile Pro Arg Pro Lys Pro Tyr Arg Asp Glu Gly
            245                 250                 255

Phe Val Arg Leu Asp Ile Lys Ala Ile Lys Gly Leu Glu Ile Leu Glu
            260                 265                 270

Ser Leu Glu Gly Arg Lys Asp Ile Ser Leu Phe Lys Val Ile Asp Arg
        275                 280                 285

Thr Leu Thr Gly Met Gly Arg Arg Arg Leu Lys Phe Arg Leu Leu Ser
    290                 295                 300

Pro Phe Arg Ser Arg Glu Lys Ile Glu Arg Ile Gln Glu Gly Val Gln
305                 310                 315                 320

Glu Leu Lys Glu Asn Arg Glu Ala Leu Leu Lys Ile Arg Gln Ile Leu
            325                 330                 335

Glu Gly Met Ala Asp Leu Glu Arg Leu Val Ser Lys Ile Ser Ser Asn
            340                 345                 350

Met Ala Thr Pro Arg Glu Leu Val Tyr Leu Lys Asn Ser Leu Lys Lys
        355                 360                 365

-continued

```
Val Glu Glu Leu Arg Leu Leu Leu Glu Leu Lys Ala Pro Ile Phe
370             375             380

Lys Glu Ile Leu Gln Asn Phe Glu Asp Thr Lys Lys Ile Ile Asn Asp
385             390             395             400

Ile Glu Lys Thr Leu Val Glu Asp Pro Pro Leu His Val Lys Glu Gly
                405             410             415

Gly Leu Ile Arg Glu Gly Val Asn Ala Tyr Leu Asp Glu Leu Arg Phe
                420             425             430

Ile Arg Asp Asn Ala Glu Thr Tyr Leu Arg Glu Tyr Glu Lys Lys Leu
        435             440             445

Arg Gln Glu Thr Gly Ile Gln Ser Leu Lys Ile Gly Tyr Asn Lys Val
    450             455             460

Met Gly Tyr Tyr Ile Glu Val Thr Lys Pro Asn Leu Lys Tyr Val Pro
465             470             475             480

Ser Tyr Phe Arg Arg Arg Gln Thr Leu Ser Asn Ser Glu Arg Phe Thr
                485             490             495

Thr Glu Glu Leu Gln Arg Leu Glu Glu Lys Ile Leu Ser Ala Gln Thr
            500             505             510

Arg Ile Asn Asp Leu Glu Tyr Glu Leu Tyr Lys Glu Leu Arg Glu Arg
        515             520             525

Val Val Lys Glu Leu Asp Lys Val Gly Asn Asn Ala Ser Ala Val Ala
    530             535             540

Glu Val Asp Phe Ile Gln Ser Leu Ala Gln Ile Ala Tyr Glu Lys Asp
545             550             555             560

Trp Ala Lys Pro Gln Ile His Glu Gly Tyr Glu Leu Ile Ile Glu Glu
                565             570             575

Gly Arg His Pro Val Ile Glu Glu Phe Val Glu Asn Tyr Val Pro Asn
            580             585             590

Asp Thr Lys Leu Asp Arg Asp Ser Phe Ile His Val Ile Thr Gly Pro
        595             600             605

Asn Met Ala Gly Lys Ser Ser Tyr Ile Arg Gln Val Gly Val Leu Thr
    610             615             620

Leu Leu Ser His Ile Gly Ser Phe Ile Pro Ala Arg Arg Ala Lys Ile
625             630             635             640

Pro Val Val Asp Ala Leu Phe Thr Arg Ile Gly Ser Gly Asp Val Leu
                645             650             655

Ala Leu Gly Val Ser Thr Phe Met Asn Glu Met Leu Glu Val Ser Asn
                660             665             670

Ile Leu Asn Asn Ala Thr Glu Lys Ser Leu Val Ile Leu Asp Glu Val
        675             680             685

Gly Arg Gly Thr Ser Thr Tyr Asp Gly Ile Ala Ile Ser Lys Ala Ile
    690             695             700

Val Lys Tyr Ile Ser Glu Lys Leu Lys Ala Lys Thr Leu Leu Ala Thr
705             710             715             720

His Phe Leu Glu Ile Thr Glu Leu Glu Gly Lys Ile Glu Gly Val Lys
                725             730             735

Asn Tyr His Met Glu Val Glu Lys Thr Pro Glu Gly Ile Arg Phe Leu
            740             745             750

Tyr Ile Leu Lys Glu Gly Lys Ala Glu Gly Ser Phe Gly Ile Glu Val
            755             760             765

Ala Lys Leu Ala Gly Leu Pro Glu Glu Val Val Glu Glu Ala Arg Lys
    770             775             780

Ile Leu Arg Glu Leu Glu Glu Lys Glu Asn Lys Lys Glu Asp Ile Val
```

-continued

```
       785                790                795                800
Pro Leu Leu Glu Glu Thr Phe Lys Lys Ser Glu Glu Ala Gln Arg Leu
                805                810                815

Glu Glu Tyr Glu Glu Ile Ile Lys Lys Ile Glu Glu Ile Asp Ile Gly
                820                825                830

Asn Thr Thr Pro Leu Gln Ala Leu Leu Ile Leu Ala Glu Leu Lys Lys
                835                840                845

Lys Cys Ser Phe Ser Lys Lys Glu Ser Gly Ala
        850                855

<210> SEQ ID NO 5
<211> LENGTH: 855
<212> TYPE: PRT
<213> ORGANISM: Aquifex pyrophilus

<400> SEQUENCE: 5

Met Gly Lys Glu Glu Lys Glu Leu Thr Pro Met Leu Ala Gln Tyr His
1                5                10                15

Gln Phe Lys Ser Met Tyr Pro Asp Cys Leu Leu Leu Phe Arg Leu Gly
                20                25                30

Asp Phe Tyr Glu Leu Phe Tyr Glu Asp Ala Val Val Gly Ser Lys Glu
                35                40                45

Leu Gly Leu Val Leu Thr Ser Arg Pro Ala Gly Lys Gly Arg Glu Arg
        50                55                60

Ile Pro Met Cys Gly Val Pro Tyr His Ser Ala Asn Asn Tyr Ile Ala
65                70                75                80

Lys Leu Val Asn Lys Gly Tyr Lys Val Ala Ile Cys Glu Gln Val Glu
                85                90                95

Asp Pro Ser Lys Ala Lys Gly Ile Val Lys Arg Asp Val Ile Arg Val
                100                105                110

Ile Thr Pro Gly Thr Phe Phe Glu Arg Glu Thr Gly Gly Leu Cys Ser
                115                120                125

Leu Tyr Arg Lys Gly Lys Ser Tyr Leu Val Ser Tyr Leu Asn Leu Ser
        130                135                140

Val Gly Glu Phe Ile Gly Ala Lys Val Lys Glu Glu Glu Leu Ile Asp
145                150                155                160

Phe Leu Ser Lys Phe Asn Ile Arg Glu Val Leu Val Lys Lys Gly Glu
                165                170                175

Lys Leu Pro Glu Lys Leu Glu Lys Val Leu Lys Leu His Ile Thr Glu
                180                185                190

Leu Glu Glu Glu Phe Phe Glu Glu Gly Lys Glu Glu Leu Leu Lys Asp
                195                200                205

Tyr Gly Val Pro Ser Ile Lys Ala Phe Gly Phe Gln Asp Glu Asp Leu
        210                215                220

Ser Leu Ser Leu Gly Ala Val Tyr Arg Tyr Ala Lys Ala Thr Gln Lys
225                230                235                240

Ser Phe Thr Pro Leu Ile Pro Lys Pro Lys Pro Tyr Val Asp Glu Gly
                245                250                255

Tyr Val Lys Leu Asp Leu Lys Ala Val Lys Gly Leu Glu Ile Thr Glu
                260                265                270

Ser Ile Glu Gly Arg Lys Asp Leu Ser Leu Phe Lys Val Val Asp Arg
        275                280                285

Thr Leu Thr Gly Met Gly Arg Arg Arg Leu Arg Phe Arg Leu Leu Asn
        290                295                300
```

-continued

```
Pro Phe Arg Ser Ile Glu Arg Ile Arg Lys Val Gln Glu Ala Val Glu
305             310             315             320

Glu Leu Ile Asn Lys Arg Glu Val Leu Asn Glu Ile Arg Lys Thr Leu
            325             330             335

Glu Gly Met Ser Asp Leu Glu Arg Leu Val Ser Arg Ile Ser Ser Asn
            340             345             350

Met Ala Ser Pro Arg Glu Leu Ile His Leu Lys Asn Ser Leu Arg Lys
            355             360             365

Ala Glu Glu Leu Arg Lys Ile Leu Ser Leu Leu Asp Ser Glu Ile Phe
    370             375             380

Lys Glu Ile Glu Gly Ser Leu Leu Asn Leu Asn Lys Val Ala Asp Leu
385             390             395             400

Ile Asp Lys Thr Leu Val Asp Asp Pro Pro Leu His Val Lys Glu Gly
            405             410             415

Gly Leu Ile Lys Pro Gly Val Asn Ala Tyr Leu Asp Glu Leu Arg Phe
            420             425             430

Ile Arg Glu Asn Ala Glu Lys Leu Leu Lys Glu Tyr Glu Lys Lys Leu
    435             440             445

Lys Lys Glu Thr Gly Ile Gln Ser Leu Lys Ile Gly Tyr Asn Lys Val
    450             455             460

Met Gly Tyr Tyr Ile Glu Val Thr Lys Ala Asn Val Lys Tyr Val Pro
465             470             475             480

Glu His Phe Arg Arg Arg Gln Thr Leu Ser Asn Ala Glu Arg Tyr Thr
            485             490             495

Thr Glu Glu Leu Gln Arg Leu Glu Glu Lys Ile Leu Ser Ala Gln Thr
            500             505             510

Arg Ile Asn Glu Leu Glu Tyr Glu Leu Tyr Arg Glu Leu Arg Glu Glu
    515             520             525

Val Val Lys Glu Leu Asp Lys Val Gly Asn Asn Ala Thr Leu Ile Gly
    530             535             540

Glu Val Asp Tyr Ile Gln Ser Leu Ala Trp Leu Ala Leu Glu Lys Gly
545             550             555             560

Trp Val Lys Pro Glu Val His Glu Gly Tyr Glu Leu Ile Ile Glu Glu
            565             570             575

Gly Lys His Pro Val Ile Glu Glu Phe Thr Lys Asn Tyr Val Pro Asn
            580             585             590

Asp Thr Lys Leu Thr Glu Glu Glu Phe Ile His Val Ile Thr Gly Pro
    595             600             605

Asn Met Ala Gly Lys Ser Ser Tyr Ile Arg Gln Val Gly Val Leu Thr
    610             615             620

Leu Leu Ala His Thr Gly Ser Phe Leu Pro Val Lys Ser Ala Arg Ile
625             630             635             640

Pro Leu Val Asp Ala Ile Phe Thr Arg Ile Gly Ser Gly Asp Val Leu
            645             650             655

Ala Leu Gly Val Ser Thr Phe Met Asn Glu Met Leu Asp Val Ser Asn
            660             665             670

Ile Leu Asn Asn Ala Thr Lys Arg Ser Leu Ile Ile Leu Asp Glu Val
    675             680             685

Gly Arg Gly Thr Ser Thr Tyr Asp Gly Ile Ala Ile Ser Lys Ala Ile
    690             695             700

Val Lys Tyr Ile Ser Glu Lys Ile Gly Ala Lys Thr Leu Leu Ala Thr
705             710             715             720

His Tyr Leu Glu Leu Thr Glu Leu Glu Arg Lys Val Lys Gly Val Lys
```

-continued

```
                    725                 730                 735
Asn Tyr His Met Glu Val Glu Glu Thr Asp Glu Gly Ile Arg Phe Leu
            740                 745                 750

Tyr Ile Leu Lys Glu Gly Arg Ala Lys Gly Ser Phe Gly Ile Asp Val
            755                 760                 765

Ala Lys Leu Ala Gly Leu Pro Glu Glu Val Val Arg Glu Ala Lys Lys
    770                 775                 780

Ile Leu Lys Glu Leu Glu Gly Glu Lys Gly Lys Gln Glu Val Leu Pro
785                 790                 795                 800

Phe Leu Glu Glu Thr Tyr Lys Lys Ser Val Asp Glu Glu Lys Leu Asn
                805                 810                 815

Phe Tyr Glu Glu Ile Ile Lys Glu Ile Glu Glu Ile Asp Ile Gly Asn
            820                 825                 830

Thr Thr Pro Val Lys Ala Leu Leu Ile Leu Ala Glu Leu Lys Glu Arg
            835                 840                 845

Ile Lys Ser Phe Ile Lys Arg
    850                 855

<210> SEQ ID NO 6
<211> LENGTH: 793
<212> TYPE: PRT
<213> ORGANISM: Thermotoga maritima

<400> SEQUENCE: 6

Met Lys Val Thr Pro Leu Met Glu Gln Tyr Leu Arg Ile Lys Glu Gln
1               5                   10                  15

Tyr Lys Asp Ser Ile Leu Leu Phe Arg Leu Gly Asp Phe Tyr Glu Ala
            20                  25                  30

Phe Phe Glu Asp Ala Lys Ile Val Ser Lys Val Leu Asn Ile Val Leu
            35                  40                  45

Thr Arg Arg Gln Asp Ala Pro Met Ala Gly Ile Pro Tyr His Ala Leu
        50                  55                  60

Asn Thr Tyr Leu Lys Lys Leu Val Glu Ala Gly Tyr Lys Val Ala Ile
65                  70                  75                  80

Cys Asp Gln Met Glu Glu Pro Ser Lys Ser Lys Lys Leu Ile Arg Arg
                85                  90                  95

Glu Val Thr Arg Val Val Thr Pro Gly Ser Ile Val Glu Asp Glu Phe
            100                 105                 110

Leu Ser Glu Thr Asn Asn Tyr Met Ala Val Val Ser Glu Glu Lys Gly
            115                 120                 125

Arg Tyr Cys Thr Val Phe Cys Asp Val Ser Thr Gly Glu Val Leu Val
        130                 135                 140

His Glu Ser Ser Asp Glu Gln Glu Thr Leu Asp Leu Leu Lys Asn Tyr
145                 150                 155                 160

Ser Ile Ser Gln Ile Ile Cys Pro Glu His Leu Lys Ser Ser Leu Lys
                165                 170                 175

Glu Arg Phe Pro Gly Val Tyr Thr Glu Thr Ile Ser Glu Trp Tyr Phe
            180                 185                 190

Ser Asp Leu Glu Glu Val Glu Lys Ala Tyr Asn Leu Lys Asp Ile His
        195                 200                 205

His Phe Glu Leu Ser Pro Leu Ala Leu Lys Ala Leu Ala Ala Leu Ile
    210                 215                 220

Lys Tyr Val Lys Tyr Thr Met Ile Gly Glu Asp Leu Asn Leu Lys Pro
225                 230                 235                 240
```

```
Pro Leu Leu Ile Ser Gln Arg Asp Tyr Met Ile Leu Asp Ser Ala Thr
            245                 250                 255

Val Glu Asn Leu Ser Trp Ile Pro Gly Asp Arg Gly Lys Asn Leu Phe
            260                 265                 270

Asp Val Leu Asn Asn Thr Glu Thr Pro Met Gly Ala Arg Leu Gly Lys
            275                 280                 285

Lys Trp Ile Leu His Pro Leu Val Asp Arg Lys Gln Ile Glu Glu Arg
    290                 295                 300

Leu Lys Ala Val Glu Arg Leu Val Asn Asp Arg Val Ser Leu Glu Glu
305                 310                 315                 320

Met Arg Asn Leu Leu Ser Asn Val Arg Asp Val Glu Arg Ile Val Ser
                325                 330                 335

Arg Val Glu Tyr Asn Arg Ser Val Pro Arg Asp Leu Val Ala Leu Arg
                340                 345                 350

Glu Thr Leu Glu Ile Ile Pro Lys Leu Asn Glu Val Leu Ser Thr Phe
            355                 360                 365

Gly Val Phe Lys Lys Leu Ala Phe Pro Glu Gly Leu Val Asp Leu Leu
    370                 375                 380

Arg Lys Ala Ile Glu Asp Asp Pro Val Gly Ser Pro Gly Glu Gly Lys
385                 390                 395                 400

Val Ile Lys Arg Gly Phe Ser Ser Glu Leu Asp Glu Tyr Arg Asp Leu
                405                 410                 415

Leu Glu His Ala Glu Glu Arg Leu Lys Glu Phe Glu Glu Lys Glu Arg
                420                 425                 430

Glu Arg Thr Gly Ile Gln Lys Leu Arg Val Gly Tyr Asn Gln Val Phe
            435                 440                 445

Gly Tyr Tyr Ile Glu Val Thr Lys Ala Asn Leu Asp Lys Ile Pro Asp
    450                 455                 460

Asp Tyr Glu Arg Lys Gln Thr Leu Val Asn Ser Glu Arg Phe Ile Thr
465                 470                 475                 480

Pro Glu Leu Lys Glu Phe Glu Thr Lys Ile Met Ala Ala Lys Glu Arg
                485                 490                 495

Ile Glu Glu Leu Glu Lys Glu Leu Phe Thr Ser Val Cys Glu Glu Val
            500                 505                 510

Lys Lys His Lys Glu Val Leu Leu Glu Ile Ser Glu Asp Leu Ala Lys
        515                 520                 525

Ile Asp Ala Leu Ser Thr Leu Ala Tyr Asp Ala Ile Met Tyr Asn Tyr
    530                 535                 540

Thr Lys Pro Val Phe Ser Glu Asp Arg Leu Glu Ile Lys Gly Gly Arg
545                 550                 555                 560

His Pro Val Val Glu Arg Phe Thr Gln Asn Phe Val Glu Asn Asp Ile
                565                 570                 575

Tyr Met Asp Asn Glu Lys Arg Phe Val Val Ile Thr Gly Pro Asn Met
            580                 585                 590

Ser Gly Lys Ser Thr Phe Ile Arg Gln Val Gly Leu Ile Ser Leu Met
        595                 600                 605

Ala Gln Ile Gly Ser Phe Val Pro Ala Gln Lys Ala Ile Leu Pro Val
    610                 615                 620

Phe Asp Arg Ile Phe Thr Arg Met Gly Ala Arg Asp Asp Leu Ala Gly
625                 630                 635                 640

Gly Arg Ser Thr Phe Leu Val Glu Met Asn Glu Met Ala Leu Ile Leu
                645                 650                 655

Leu Lys Ser Thr Asn Lys Ser Leu Val Leu Leu Asp Glu Val Gly Arg
```

-continued

```
              660                    665                    670

Gly Thr Ser Thr Gln Asp Gly Val Ser Ile Ala Trp Ala Ile Ser Glu
        675              680                    685

Glu Leu Ile Lys Arg Gly Cys Lys Val Leu Phe Ala Thr His Phe Thr
    690              695                    700

Glu Leu Thr Glu Leu Glu Lys His Phe Pro Gln Val Gln Asn Lys Thr
705              710              715                    720

Ile Leu Val Lys Glu Glu Gly Lys Asn Val Ile Phe Thr His Lys Val
                725              730              735

Val Asp Gly Val Ala Asp Arg Ser Tyr Gly Ile Glu Val Ala Lys Ile
            740              745              750

Ala Gly Ile Pro Asp Arg Val Ile Asn Arg Ala Tyr Glu Ile Leu Glu
        755              760              765

Arg Asn Phe Lys Asn Asn Thr Lys Lys Asn Gly Lys Ser Asn Arg Phe
    770              775              780

Ser Gln Gln Ile Pro Leu Phe Pro Val
785              790
```